(12) United States Patent
Horwitz et al.

(10) Patent No.: US 6,939,544 B2
(45) Date of Patent: Sep. 6, 2005

(54) ANTIBODIES AGAINST MOUSE PITUITARY TUMOR TRANSFORMING GENE CARBOXY-TERMINAL (PTTG-C) PEPTIDES

(75) Inventors: Gregory A. Horwitz, Calabasas, CA (US); Xun Zhang, Malden, MA (US); Shlomo Melmed, Los Angeles, CA (US)

(73) Assignee: Cedars-Sinai Medical Center, Los Angeles, CA (US)

(*) Notice: Subject to any disclaimer, the term of this patent is extended or adjusted under 35 U.S.C. 154(b) by 135 days.

(21) Appl. No.: 10/262,252

(22) Filed: Sep. 30, 2002

(65) Prior Publication Data

US 2003/0152573 A1 Aug. 14, 2003

Related U.S. Application Data

(60) Division of application No. 09/569,956, filed on May 12, 2000, which is a continuation-in-part of application No. 08/894,251, filed as application No. PCT/US97/21463 on Nov. 21, 1997, now Pat. No. 6,455,305.
(60) Provisional application No. 60/031,338, filed on Nov. 21, 1996.

(51) Int. Cl.[7] ..................... A61K 39/395; A61K 39/40; A61K 39/42
(52) U.S. Cl. ............... 424/141.1; 424/130.1; 424/134.1; 424/139.1
(58) Field of Search ............ 424/130.1, 134.1, 424/139.1, 141.1, 155.1

(56) References Cited

FOREIGN PATENT DOCUMENTS

| WO | WO 90/09442 | 8/1990 |
|---|---|---|
| WO | WO 93/25712 | 12/1993 |
| WO | WO 98/22587 | 5/1998 |

OTHER PUBLICATIONS

Wang et al., Feb. 2000, Endocrinology, vol. 141, No. 2, p. 763–771.*
Wang et al., Mar. 2000, Journal of Biological Chemistry, vol. 275, No. 11, p. 7459–7461.*
PCT International Search Report—PCT/US 97/21463, Nov. 22, 1997.
Marra, M., et al., "The WashU–HHMI Mouse EST project, AC W81747", EMBL Database, Jun. 27, 1996, Heidelberg, XP002066845.
Hillier, L., et al., The WashU–Merck EST project, AC AA007646, EMBL Database, Jul. 28, 1996, Heidelberg, XP002066846.
Holton, T., et al., "ACQ57612", EMBL Database, Sep. 5, 1994, Heidelberg, XP002066847.
Nippon Telegraph and Telephone Corp.: "ACQ75553", EMBL Database, Aug. 4, 1995, Heidelberg, XP002066848.
Goosky, R., et al., "Transforming DNA Sequences Present in Human Prolactin–Secreting Pituitary Tumors", Molec. Endocrin., 5(11): 1687–1695, Nov. 1991.

Pei, L., et al., "Isolation and Characterization of a Pituitary Tumor–Transforming Gene (PTTG)", Molec. Endocrin., 11(4): 433–441, Apr. 1997.
Shimon, L., et al., "Genetic Basis of Endocrine Disease", J. Clin. Endocrin. And Metab., 82(6): 1675–1681, Jun. 1997.
Chen, L., et al., "Identification of the human pituitary tumor transforming gene (hPTTG) family: molecular structure, expression, and chromosomal localization.", 1: Gene 2000, May 2; 248(102): 41–50, Abstract Only.
Heaney, A.P., "Expression of pituitary–tumor transforming gene in colorectal tumours", 1: Lancet 2000 Feb. 26; 355(9205): 716–9.
Heaney, A.P., "Early Involvement of Estrogen–induced pituitary tumor transforming gene and fibroblast growth factor expression in prolactinoma pathogenesis", 1: Nat Med Nov. 1999, 5(11): 1317–21.
Suhardja, A.S., et al., "Molecular pathogenesis of pituitary adenomas: a review,", Acta Neurochir (Wien) 1999; 141(7): 729–36, Abstract Only.
Ren, R., et al., "Identification of a ten–amino acid proline–rich SH3 binding site", Science Feb 19, 1993; 259(5098): 1157–61. Abstract Only.
Liu, X., et al., "The v–Sre SH3 domain binds phosphatidylinositol 3'–kinase", Mol Cell Biol Sep. 1993; 13(9): 5225–32. Abstract Only.
Gout, L., et al., "The GTPase dynamin binds to and is activated by a subset of SH3 domains." Cel Oct. 8, 1993; 75(1): 25–36.
Yu, H., et al., "Solution structure of the SH3 domain of Sre and identification of its Ugan–binding site." Science Dec. 4, 1992; 258(5088): 1665–8, Abstract Only.
Lee, I.A., et al., "Cloning and expression of human cDNA encoding human homologue of pituitary tumor transforming gene", Biochem Mol. Biol Int May 1999; 47(5): 891–7, Abstract Only.
Zou, H., et al., "Identification of a vertebrate sister–chromatid separation inhibitor involved in transformation and tumorigenesis", Science Jul. 16, 1999; 285(5426): 418–22. Abstract Only.
Zhang, X., et al., "Pituitary tumor transforming gene (PTTG) expression in pituitary adenomas" J Clin Endocrinol Metab Feb. 1999; 84(2): 761–7.

(Continued)

*Primary Examiner*—Shin-Lin Chen
(74) *Attorney, Agent, or Firm*—Seth D. Levy; David Wright Tremaine LLP

(57) ABSTRACT

Disclosed are isolated antibodies that specifically bind a murine pituitary tumor transforming gene carboxy-terminal (PTTG-C) peptide. The inventive antibodies are useful in assays to determine levels of PTTG proteins or PTTG-C peptides present in a given sample (e.g., tissue samples, biological fluids, Western blots). The antibodies can also be used to purify PTTG proteins or PTTG-C peptides from crude cell extracts and the like. The antibodies are also considered therapeutically useful to counteract and/or supplement the biological effect of PTTG proteins in vivo.

4 Claims, 5 Drawing Sheets

OTHER PUBLICATIONS

Prezant, T.R., et al., "An intronless homolog of human proto–oncogene hPTTG is expressed in pituitary tumors; evidence for hPTTG family.", J Clin Endocrinol Metab Mar. 1999; 84(3): 1149–52.

Fujimoto, N., et al., "Establishment of an estrogen responsive rat pituitary cell sub–line MtTE–2." Endocr J Jun. 1999: 46(3): 389–96. Abstract Only.

Ramos–Morales, F., et al., "Cell cycle regulated expression and phosphorylation of hpttg proto–oncogene product", Oncogene Jan. 20, 2000; 19(3): 403–9. Abstract Only.

McCabe C.J., et al., "PTTG–a new pituitary tumour transforming gene", J Endocrinol Aug. 1999; 162(2): 163–6. Abstract Only.

Kakar, S.S., "Molecular cloning, genomic organization, and identification of the promoter for the human pituitary tumor transforming gene (PTTG).", Gene Nov. 29, 1999; 240(2): 317–24. Abstract Only.

Dominguez A., et al., "hpttg, a human homologue of rat pttg, is overexpressed in hematopolectic neoplasma. Evidence for a transcriptional activation function of hPTTG.", Oncogene Oct. 29, 1998; 17(17): 2187–93, Abstract Only.

Pei, L., "Pituitary tumor–transforming gene protein associates with ribosomal protein S10 and a novel human homologue of DnsJ in testicular cells", J Biol Chem Jan. 29, 1999; 274(5): 3151–8.

Saez, C., et al., "hpttg is over–expressed in pituitary adenomas and other primary epithelial neoplaias.", Oncogene Sep. 23, 1999; 18(39): 5473–6. Abstract Only.

Pei, L., "Genomic Organization and Identification of an enhancer element containing binding sites for multiple proteins in rat pituitary tumor–transforming gene", J Biol Chem Feb. 27, 1998; 273(9): 5219–25.

Wang, Z., et al., "Characterization of the murine pituitary tumor transforming gene (PTTG)and its promoter.", Endocrinology Feb. 2000; 141(2): 763–71.

Zhang, X., et al., "Structure, expression, and function of human pituitary tumor–transforming gene (PTTG).", Mol Endocrinol Jan. 1999; 13(1): 156–66.

Heaney, Anthony, P., et al., "Pituitary tumor transforming gene: a novel factor in pituitary tumour formation" Balliere's Clinical Endocrinology and Metabolism, vol. 13, No. 3, pp. 367–380, 1999.

Dominguez, Africa et al., *hpttg, a human homologue of rat pttg, is overexpressed in hematopoiectic neoplasmas. Evidence for a transcriptional activation function of Hpttg, Oncogene*, vol. 17, pp. 2187–2195 (1998).

XP–002193233, Chen, Leilei et al., *Identification of the human pituitary tumor transforming gene (hPTTG)family: molecular structure, expression, and chromosomal localization, Gene*, vol. 248, pp. 41–50 (2000).

XP–002186232, Wang, Zhiyong et al., *Pituitary Tumor Transforming Gene (PTTG) Transforming and Transactivation Activity, The Journal of Biological Chemistry*, vol. 275, No. 11, pp. 7459–7461 (Mar. 17, 2000).

Ohgi et al.; *Expression of Rnase Rh from Rhizopus niveus in Yeast and Characterization of the Secreted Proteins, J. Biochem,*vol. 1, pp. 775–785 (1991).

Kaye et al., *A single amino acid substitution results in a retinoblastoma protein defective in phosphorylation and oncoprotein binding, Proc. Natl. Acad. Sci.*, vol. 87, pp. 6922–6926 (1990).

Rudinger; *Characteristics of the amino acids as components of a peptide hormone sequence, Peptide Hormones*, pp. 1–7 (1976).

Crystal; *Transfer of Genes to Humans: Early Lessons and Obstacles to Success, Science*, vol. 270, pp. 404–410 (1995).

Deonarain; *Ligand–targeted receptor–mediated vectors for gene delivery, Exp. Opin. Ther. Patents*, 8(1):53–69 (1998).

Eck et al., *Gene–Based Therapy, The Pharmacological Basis of Therapeutics*, pp. 77–101 (1996).

Accession No. AAT21011 (1996).

Accession No. H66067 (1995).

* cited by examiner

SEQUENCE LISTING

<160> NUMBER OF SEQ ID NOS: 19

<210> SEQ ID NO 1
<211> LENGTH: 974
<212> TYPE: DNA
<213> ORGANISM: Rattus rattus

<400> SEQUENCE: 1

```
aattcggcac gagccaacct tgagcatctg atcctcttgg cttctccttc ctatcgctga      60
gctggtaggc tggagacagt tgtttgggtg ccaacatcaa caaacgattt ctgtagttta     120
gcgtttatga ccctggcgtg aagatttaag gtctggatta agcctgttga cttctccagc     180
tacttctaaa tttttgtgca taggtgctct ggtctctgtt gctgcttagt tcttccagcc     240
ttcctcaatg ccagttttat aatatgcagg tctctcccct cagtaatcca ggatggctac     300
tctgatcttt gttgataagg ataacgaaga gccaggcagc cgtttggcat ctaaggatgg     360
attgaagctg ggctctggtg tcaaagcctt agatgggaaa ttgcaggttt caacgccacg     420
agtcggcaaa gtgttcggtg ccccaggctt gcctaaagcc agcaggaagg ctctgggaac     480
tgtcaacaga gttactgaaa agccagtgaa gagtagtaaa cccctgcaat cgaaacagcc     540
gactctgagt gtgaaaaaga tcaccgagaa gtctactaag acacaaggct ctgctcctgc     600
tcctgatgat gcctacccag aaatagaaaa gttcttcccc ttcgatcctc tagattttga     660
gagttttgac ctgcctgaag agcaccagat ctcacttctc cccttgaatg gagtgcctct     720
catgatcctg aatgaagaga gggggcttga gaagctgctg cacctggacc cccctctccc     780
tctgcagaag cccttcctac cgtgggaatc tgatccgttg ccgtctcctc ccagcgccct     840
ctccgctctg gatgttgaat tgccgcctgt ttgttacgat gcagatattt aaacgtctta     900
ctcctttata gtttatgtaa gttgtattaa taaagcattt gtgtgtaaaa aaaaaaaaaa     960
aaactcgaga gtac                                                      974
```

<210> SEQ ID NO 2
<211> LENGTH: 199
<212> TYPE: PRT

<213> ORGANISM: Rattus rattus

<400> SEQUENCE: 2

| | | | | | | | | | | | | | | |
|---|---|---|---|---|---|---|---|---|---|---|---|---|---|---|
| Met | Ala | Thr | Leu | Ile | Phe | Val | Asp | Lys | Asp | Asn | Glu | Glu | Pro | Gly | Ser |
| 1 | | | | 5 | | | | | 10 | | | | | 15 | |
| Arg | Leu | Ala | Ser | Lys | Asp | Gly | Leu | Lys | Leu | Gly | Ser | Gly | Val | Lys | Ala |
| | | | 20 | | | | | 25 | | | | | 30 | | |
| Leu | Asp | Gly | Lys | Leu | Gln | Val | Ser | Thr | Pro | Arg | Val | Gly | Lys | Val | Phe |
| | | | 35 | | | | | 40 | | | | | 45 | | |
| Gly | Ala | Pro | Gly | Leu | Pro | Lys | Ala | Ser | Arg | Lys | Ala | Leu | Gly | Thr | Val |
| | 50 | | | | | 55 | | | | | 60 | | | | |
| Asn | Arg | Val | Thr | Glu | Lys | Pro | Val | Lys | Ser | Ser | Lys | Pro | Leu | Gln | Ser |
| 65 | | | | | 70 | | | | | 75 | | | | | 80 |
| Lys | Gln | Pro | Thr | Leu | Ser | Val | Lys | Lys | Ile | Thr | Glu | Lys | Ser | Thr | Lys |
| | | | | 85 | | | | | 90 | | | | | 95 | |
| Thr | Gln | Gly | Ser | Ala | Pro | Ala | Pro | Asp | Asp | Ala | Tyr | Pro | Glu | Ile | Glu |
| | | | 100 | | | | | 105 | | | | | 110 | | |
| Lys | Phe | Phe | Pro | Phe | Asp | Pro | Leu | Asp | Phe | Glu | Ser | Phe | Asp | Leu | Pro |
| | | 115 | | | | | 120 | | | | | 125 | | | |
| Glu | Glu | His | Gln | Ile | Ser | Leu | Leu | Pro | Leu | Asn | Gly | Val | Pro | Leu | Met |
| | 130 | | | | | 135 | | | | | 140 | | | | |
| Ile | Leu | Asn | Glu | Glu | Arg | Gly | Leu | Glu | Lys | Leu | Leu | His | Leu | Asp | Pro |
| 145 | | | | | 150 | | | | | 155 | | | | | 160 |
| Pro | Ser | Pro | Leu | Gln | Lys | Pro | Phe | Leu | Pro | Trp | Glu | Ser | Asp | Pro | Leu |
| | | | | 165 | | | | | 170 | | | | | 175 | |
| Pro | Ser | Pro | Pro | Ser | Ala | Leu | Ser | Ala | Leu | Asp | Val | Glu | Leu | Pro | Pro |
| | | | 180 | | | | | 185 | | | | | 190 | | |
| Val | Cys | Tyr | Asp | Ala | Asp | Ile | | | | | | | | | |
| | | | 195 | | | | | | | | | | | | |

<210> SEQ ID NO 3
<211> LENGTH: 779
<212> TYPE: DNA
<213> ORGANISM: Homo sapiens

<400> SEQUENCE: 3

| | | | | | |
|---|---|---|---|---|---|
| atggccgcga | gttgtggttt | aaaccaggag | tgccgcgcgt | ccgttcaccg | cggcctcaga | 60 |
| tgaatgcggc | tgttaagacc | tgcaataatc | cagaatggct | actctgatct | atgttgataa | 120 |
| ggaaaatgga | gaaccaggca | cccgtgtggt | tgctaaggat | gggctgaagc | tggggtctgg | 180 |
| accttcaatc | aaagccttag | atgggagatc | tcaagtttca | acaccacgtt | ttggcaaaac | 240 |
| gttcgatgcc | ccaccagcct | tacctaaagc | tactagaaag | gctttgggaa | ctgtcaacag | 300 |
| agctacagaa | aagtctgtaa | agaccaaggg | acccctcaaa | caaaacagc | caagcttttc | 360 |
| tgccaaaaag | atgactgaga | agactgttaa | agcaaaaagc | tctgttcctg | cctcagatga | 420 |
| tgcctatcca | gaaatagaaa | aattctttcc | cttcaatcct | ctagactttg | agagttttga | 480 |
| cctgcctgaa | gagcaccaga | ttgcgcacct | cccccttgagt | ggagtgcctc | tcatgatcct | 540 |
| tgacgaggag | agagagcttg | aaaagctgtt | tcagctgggc | cccccttcac | ctgtgaagat | 600 |
| gccctctcca | ccatgggaat | ccaatctgtt | gcagtctcct | tcaagcattc | tgtcgaccct | 660 |
| ggatgttgaa | ttgccacctg | tttgctgtga | catagatatt | taaatttctt | agtgcttcag | 720 |
| agtttgtgtg | tatttgtatt | aataaagcat | tctttaacag | ataaaaaaa | aaaaaaaa | 779 |

<210> SEQ ID NO 4

```
<211> LENGTH: 202
<212> TYPE: PRT
<213> ORGANISM: Homo sapiens

<400> SEQUENCE: 4

Met Ala Thr Leu Ile Tyr Val Asp Lys Glu Asn Gly Glu Pro Gly Thr
 1               5                  10                  15

Arg Val Val Ala Lys Asp Gly Leu Lys Leu Gly Ser Gly Pro Ser Ile
                20                  25                  30

Lys Ala Leu Asp Gly Arg Ser Gln Val Ser Thr Pro Arg Phe Gly Lys
            35                  40                  45

Thr Phe Asp Ala Pro Pro Ala Leu Pro Lys Ala Thr Arg Lys Ala Leu
        50                  55                  60

Gly Thr Val Asn Arg Ala Thr Glu Lys Ser Val Lys Thr Lys Gly Pro
 65                 70                  75                  80

Leu Lys Gln Lys Gln Pro Ser Phe Ser Ala Lys Lys Met Thr Glu Lys
                85                  90                  95

Thr Val Lys Ala Lys Ser Ser Val Pro Ala Ser Asp Ala Tyr Pro
                100                 105                 110

Glu Ile Glu Lys Phe Phe Pro Phe Asn Pro Leu Asp Phe Glu Ser Phe
            115                 120                 125

Asp Leu Pro Glu Glu His Gln Ile Ala His Leu Pro Leu Ser Gly Val
        130                 135                 140

Pro Leu Met Ile Leu Asp Glu Glu Arg Glu Leu Glu Lys Leu Phe Gln
145                 150                 155                 160

Leu Gly Pro Pro Ser Pro Val Lys Met Pro Ser Pro Pro Trp Glu Ser
                165                 170                 175

Asn Leu Leu Gln Ser Pro Ser Ser Ile Leu Ser Thr Leu Asp Val Glu
                180                 185                 190

Leu Pro Pro Val Cys Cys Asp Ile Asp Ile
            195                 200

<210> SEQ ID NO 5
<211> LENGTH: 31
<212> TYPE: DNA
<213> ORGANISM: Artificial Sequence
<220> FEATURE:
<223> OTHER INFORMATION: Synthetic oligonucleotide.

<400> SEQUENCE: 5
gatgctctcc gcactctggg aatccaatct g                                    31

<210> SEQ ID NO 6
<211> LENGTH: 32
<212> TYPE: DNA
<213> ORGANISM: Artificial Sequence
<220> FEATURE:
<223> OTHER INFORMATION: Synthetic oligonucleotide.

<400> SEQUENCE: 6
ttcacaagtt gagggcgcc cagctgaaac ag                                    32

<210> SEQ ID NO 7
<211> LENGTH: 32
<212> TYPE: DNA
<213> ORGANISM: Artificial Sequence
<220> FEATURE:
<223> OTHER INFORMATION: Synthetic oligonucleotide specific to pCI-neo
      plasmid. vector.

<400> SEQUENCE: 7
```

```
ggctagagta cttaatacga ctcactatag gc                                   32
```

<210> SEQ ID NO 8
<211> LENGTH: 31
<212> TYPE: DNA
<213> ORGANISM: Homo sapiens

<400> SEQUENCE: 8

```
ctatgtcaca gcaaacaggt ggcaattcaa c                                    31
```

<210> SEQ ID NO 9
<211> LENGTH: 56
<212> TYPE: PRT
<213> ORGANISM: Homo sapiens

<400> SEQUENCE: 9

```
Met Ile Leu Asp Glu Glu Arg Glu Leu Glu Lys Leu Phe Gln Leu Gly
 1               5                  10                  15

Pro Pro Ser Pro Val Lys Met Pro Ser Pro Trp Glu Ser Asn Leu
             20                  25                  30

Leu Gln Ser Pro Ser Ser Ile Leu Ser Thr Leu Asp Val Glu Leu Pro
         35                  40                  45

Pro Val Cys Cys Asp Ile Asp Ile
     50                  55
```

<210> SEQ ID NO 10
<211> LENGTH: 168
<212> TYPE: DNA
<213> ORGANISM: Homo sapiens

<400> SEQUENCE: 10

```
atgatccttg acgaggagag agagcttgaa aagctgtttc agctgggccc cccttcacct      60
gtgaagatgc cctctccacc atgggaatcc aatctgttgc agtctccttc aagcattctg     120
tcgaccctgg atgttgaatt gccacctgtt tgctgtgaca tagatatt                  168
```

<210> SEQ ID NO 11
<211> LENGTH: 16
<212> TYPE: DNA
<213> ORGANISM: Artificial Sequence
<220> FEATURE:
<223> OTHER INFORMATION: Anchored primer sequence.

<400> SEQUENCE: 11

```
aagctttttt tttttg                                                     16
```

<210> SEQ ID NO 12
<211> LENGTH: 13
<212> TYPE: DNA
<213> ORGANISM: Artificial Sequence
<220> FEATURE:
<223> OTHER INFORMATION: Arbitrary primer sequence.

<400> SEQUENCE: 12

```
aagcttgctg ctc                                                        13
```

<210> SEQ ID NO 13
<211> LENGTH: 16
<212> TYPE: DNA
<213> ORGANISM: Artificial Sequence
<220> FEATURE:
<223> OTHER INFORMATION: n = a, g, or c; Anchored primer sequence.

<400> SEQUENCE: 13
aagctttttt tttttn                                                          16

<210> SEQ ID NO 14
<211> LENGTH: 194
<212> TYPE: PRT
<213> ORGANISM: Mus musculus

<400> SEQUENCE: 14

```
Met Ala Thr Leu Ile Phe Val Asp Lys Asp Asn Glu Glu Pro Gly Arg
 1               5                  10                  15

Arg Leu Ala Ser Lys Asp Gly Leu Lys Leu Gly Thr Gly Val Lys Ala
             20                  25                  30

Leu Asp Gly Lys Leu Gln Val Ser Thr Pro Arg Val Gly Lys Val Phe
         35                  40                  45

Asn Ala Pro Ala Val Pro Lys Ala Ser Arg Lys Ala Leu Gly Thr Val
     50                  55                  60

Asn Arg Val Ala Glu Lys Pro Met Lys Thr Gly Lys Pro Leu Gln Pro
 65                  70                  75                  80

Lys Gln Pro Thr Leu Thr Gly Lys Lys Ile Thr Glu Lys Ser Thr Lys
                 85                  90                  95

Thr Gln Ser Ser Val Pro Ala Pro Asp Asp Ala Tyr Pro Glu Ile Glu
                100                 105                 110

Lys Phe Phe Pro Phe Asn Pro Leu Asp Phe Asp Leu Pro Glu Glu His
            115                 120                 125

Gln Ile Ser Leu Leu Pro Leu Asn Gly Val Pro Leu Ile Thr Leu Asn
        130                 135                 140

Glu Glu Arg Gly Leu Glu Lys Leu Leu His Leu Gly Pro Pro Ser Pro
145                 150                 155                 160

Leu Lys Thr Pro Phe Leu Ser Trp Glu Ser Asp Pro Lys Pro Pro Ser
                165                 170                 175

Ala Leu Ser Thr Leu Asp Val Glu Leu Pro Pro Val Cys Tyr Asp Ala
            180                 185                 190

Asp Ile
```

<210> SEQ ID NO 15
<211> LENGTH: 945
<212> TYPE: DNA
<213> ORGANISM: Mus musculus

<400> SEQUENCE: 15
tcttgaactt gttatgtagc aggaggccaa atttgagcat cctcttggct tctctttata      60
gcagagattg taggctggag acagttttga tgggtgccaa cataaactga tttctgtaag     120
agttgagtgt tttatgaccc tggcgtgcag atttaggatc tggattaagc ctgttgactt     180
ctccagctac ttataaattt ttgtgcatag gtgccctggg taaagcttgg tctctgttac     240
tgcgtagttt ttccagccgt ctcaatgcca atattcaggc tctctcccct agagtaatcc     300
agaatggcta ctcttatctt tgttgataag gataatgaag aacccggccg ccgtttggca     360
tctaaggatg ggttgaagct gggcactggt gtcaaggcct tagatgggaa attgcaggtt     420
tcaacgcctc gagtcggcaa agtgttcaat gctccagccg tgcctaaagc cagcagaaag     480
gctttgggga cagtcaacag agttgccgaa aagcctatga agactggcaa acccctccaa     540
ccaaaacagc cgaccttgac tgggaaaaag atcaccgaga gtctactaa gacacaaagc      600
tctgttcctg ctcctgatga tgcctaccca gaaatagaaa agttcttccc tttcaatcct     660

```
ctagattttg acctgcctga ggagcaccag atctcacttc tccccttgaa tggcgtgcct    720
ctcatcaccc tgaatgaaga gagagggctg agaagctgc tgcatctggg ccccctagc     780 cctctgaaga cacccttcct atcatgggaa tctgatccgc tgtactctcc tcccagtgcc    840
ctctccactc tggatgttga attgccgcct gtttgttacg atgcagatat ttaaacttct    900
tacttctttg tagtttctgt atgtatgttg tattaataaa gcatt                    945

<210> SEQ ID NO 16
<211> LENGTH: 56
<212> TYPE: PRT
<213> ORGANISM: Rattus rattus

<400> SEQUENCE: 16

Met Ile Leu Asn Glu Glu Arg Gly Leu Glu Lys Leu Leu His Leu Asp
 1               5                  10                  15

Pro Pro Ser Pro Leu Gln Lys Pro Phe Leu Pro Trp Glu Ser Asp Pro
            20                  25                  30

Leu Pro Ser Pro Pro Ser Ala Leu Ser Ala Leu Asp Val Glu Leu Pro
        35                  40                  45

Pro Val Cys Tyr Asp Ala Asp Ile
    50                  55

<210> SEQ ID NO 17
<211> LENGTH: 56
<212> TYPE: PRT
<213> ORGANISM: Mus musculus

<400> SEQUENCE: 17

Ile Thr Leu Asn Glu Glu Arg Gly Leu Glu Lys Leu Leu His Leu Gly
 1               5                  10                  15

Pro Pro Ser Pro Leu Lys Thr Pro Phe Leu Ser Trp Glu Ser Asp Pro
            20                  25                  30

Leu Tyr Ser Pro Pro Ser Ala Leu Ser Thr Leu Asp Val Glu Leu Pro
        35                  40                  45

Pro Val Cys Tyr Asp Ala Asp Ile
    50                  55

<210> SEQ ID NO 18
<211> LENGTH: 168
<212> TYPE: DNA
<213> ORGANISM: Rattus rattus

<400> SEQUENCE: 18
atgatcctga tgaagagag ggggcttgag aagctgctgc acctggaccc cccttcccct     60
ctgcagaagc ccttcctacc gtgggaatct gatccgttgc cgtctcctcc cagcgccctc   120
tccgctctgg atgttgaatt gccgcctgtt tgttacgatg cagatatt                168

<210> SEQ ID NO 19
<211> LENGTH: 168
<212> TYPE: DNA
<213> ORGANISM: Mus musculus

<400> SEQUENCE: 19
atcaccctga tgaagagag agggctggag aagctgctgc atctgggccc cctagcccct     60
ctgaagacac cctttctatc atgggaatct gatccgctgt actctcctcc cagtgccctc   120
tccactctgg atgttgaatt gccgcctgtt tgttacgatg cagatatt                168
```

US 6,939,544 B2

ANTIBODIES AGAINST MOUSE PITUITARY TUMOR TRANSFORMING GENE CARBOXY-TERMINAL (PTTG-C) PEPTIDES

This application is a division of U.S. Non-provisional Application Ser. No. 09/569,956, filed on May 12, 2000, which is a continuation-in-part of U.S. Ser. No. 08/894,251, filed on Jul. 23, 1999 and issued as U.S. Pat. No. 6,455,305 on Sep. 24, 2002, as a national stage application, under 35 U.S.C. § 371, of international application PCT/US97/21463, filed Nov. 21, 1997, which claims the priority of the filing date of U.S. Provisional Application Ser. No. 60/031,338, filed Nov. 21, 1996.

The U.S. Government has a paid-up license in this invention and the right in limited circumstances to require the patent owner to license others on reasonable terms as provided for by the terms of Contract CA75979, awarded by the National Cancer Institute of the National Institutes of Health.

BACKGROUND OF THE INVENTION

Throughout the application various publications are referenced in parentheses. The disclosures of these publications in their entireties are hereby incorporated by reference in the application in order to more fully describe the state of the art to which this invention pertains.

1. Field of the Invention

The present invention relates to a method of inhibiting neoplastic cellular proliferation and/or transformation of mammalian cells, in vitro and in vivo.

2. Related Art

Neoplasms, including cancers and other tumors, are the second most prevalent cause of death in the United States, causing 450,000 deaths per year. One in three Americans will develop cancer, and one in five will die of cancer (Scientific American Medicine, part 12, I, 1, section dated 1987). While substantial progress has been made in identifying some of the likely environmental and hereditary causes of cancer, the statistics for the cancer death rate indicates a need for substantial improvement in the therapy for cancer and related diseases and disorders.

A number of cancer genes, i.e., genes that have been implicated in the etiology of cancer, have been identified in connection with hereditary forms of cancer and in a large number of well-studied tumor cells. Studies of cancer genes have helped provide some understanding of the process of tumorigenesis. While a great deal more remains to be learned about cancer genes, the presently known cancer genes serve as useful models for understanding tumorigenesis.

Cancer genes are broadly classified into "oncogenes" which, when activated, promote tumorigenesis, and "tumor suppressor genes" which, when damaged, fail to suppress tumorigenesis. While these classifications provide a useful method for conceptualizing tumorigenesis, it is also possible that a particular gene may play differing roles depending upon the particular allelic form of that gene, its regulatory elements, the genetic background and the tissue environment in which it is operating.

More than 100 oncogenes have been discovered, but only a small percentage appear mutated in tumors. (Bishop, J. M., *Molecular themes in oncogenesis*, Cell 64:235–248 [1991]; Sager, R., *Expression genetics in cancer: shifting the focus from DNA to XNA*, Proc. Natl. Acad Sci. 94:952–955 [1997]). Most cancer-related genes exhibit altered expression patterns (increasing or decreasing), causing phenotypic changes involving signal transduction, cell proliferation, DNA repair, angiogenesis, and apoptosis. (Pawson, T., and Hunter, T., *Signal transduction and growth control in normal and cancer cells*, Curr. Opin Gene Dev. 4:1–4 [1994]; Bartek, J., et al., *Defects in cell cycle control and cancer*, J Pathol, 187:95–99 [1999]; Sancer, A., *Mechanisms of DNA excision repair*, Science 266: 1954–1956 [1994]; Hanahan, D., and Folkman, J., *Pattern and emerging mechanisms of the angiogenic switch during tumorigenesis*, Cell 86:353–346 [1996]; Wyllie, A. H., *The genetic regulation of apoptosis*, Curr, Opin. Gene Dev. 5:97–104 [1995]). Identifying specific regulators modulating oncogene expression is important to provide the basis for development of potential subcellular therapeutic strategies. (Gibbs, J. B., and Oliff A., *Pharmaceutical research in molecular oncology*, Cell 79:193–198 [1994]; Levitzki A., *Signal-transduction therapy: a novel approach to disease management*, Eur. J. Biochem. 226:1–13 [1994]).

Tumor suppressor genes play a role in regulating oncogenesis. Tumor suppressor genes are genes that in their wild-type alleles, express proteins that suppress abnormal cellular proliferation. When the gene coding for a tumor suppressor protein is mutated or deleted, the resulting mutant protein or the complete lack of tumor suppressor protein expression may fail to correctly regulate cellular proliferation, and abnormal cellular proliferation may take place, particularly if there is already existing damage to the cellular regulatory mechanism. A number of well-studied human tumors and tumor cell lines have been shown to have missing or nonfunctional tumor suppressor genes. Examples of tumor suppressor genes include, but are not limited to the retinoblastoma susceptibility gene or RB gene, the p53 gene, the deleted in colon carcinoma (DDC) gene and the neurofibromatosis type 1 (NF-1) tumor suppressor gene (Weinberg, R. A., Science, 254:1138–46 [1991]). Loss of function or inactivation of tumor suppressor genes may play a central role in the initiation and/or progression of a significant number of human cancers.

Anterior pituitary tumors are mostly benign hormone-secreting or non-functioning adenomas arising from a monoclonal expansion of a genetically mutated pituitary epithelial cell. Pathogenesis of tumor formation in the anterior pituitary has been intensively studied. Mechanisms for pituitary tumorigenesis involve a multi-step cascade of recently characterized molecular events. The most well characterized oncogene in pituitary tumors is gsp; a constitutively activated G(s)α protein results from certain point mutations in gsp. (E.g., Fragoso, M. C., et al., *Activating mutation of the stimulatory G protein [gsp] as a putative cause of ovarian and testicular human stromal Leydig cell tumors*, J. Clin. Endocrinol. 83(6):2074–78 [1999]; Barlier, A. et al., *Impact of gsp oncogene on the expression of genes coding for Gsalpha, Pit-1, Gi2alpha, and somatostatin receptor 2 in human somatotroph adenomas: involvement of octreotide sensitivity*, J. Clin. Endocrinol. Metab. 84(8):2759–65 [1999]; Ballare, E., et al., *Activating mutations of the Gs alpha gene are associated with low levels of Gs alpha protein in growth hormone-secreting tumors*, J. Clin. Endocrinol. Metab. 83(12):4386–90 [1999]).

G(s)α mutations occur in about 40% of growth hormone (GH)-secreting tumors, and constitutively activated CREB transcription factor is also found in a subset of these tumors. Although the importance of GSα mutant proteins in the development of growth-hormone secreting pituitary tumors is well established, only about one third of these tumors contains these mutations, indicating the presence of additional transforming events in pituitary tumorigenesis. Although point mutations of Ras oncogene, loss of heterozygosity (LOH) near the Rb locus on chromosome 13, and LOH on chromosome 11 have been implicated in some pituitary tumors, the mechanism that causes pituitary cell transformation remains largely unknown.

Recently, a novel pituitary tumor transforming gene, PTTG (previously known as pituitary-tumor-specific-gene [PTSG]), was isolated. PTTG encodes a securin protein the expression of which causes cell transformation, induces the production of basic fibroblast growth factor (bFGF), is regulated in vitro and in vivo by estrogen, and inhibits chromatid separation. (Pei, L., and Melmed S., *Isolation and characterization of a pituitary tumor transforming gene*, Mol. Endocrinol. 11:433–441 [1997]; Zhang, X., et al., *Structure, expression, and function of human pituitary tumor-transforming gene (PTTG)*, Mol. Endocrinol. 13:156–166 [1999a]; Heaney, A. P., et al., *Early involvement of estrogen-induced pituitary tumor transforming gene and fibroblast growth factor expression in prolactinoma pathogenesis*, Nature Med. 5:1317–1321 [1999]; Zou, H., et al., *Identification of a vertebrate sister-chromatid separation inhibitor involved in transformation and turnorigenesis*, Science 285:418–422 [1999]).

By dysregulating chromatid separation, PTTG overexpression may also lead to aneuploidy, i.e., cells having one or a few chromosomes above or below the normal chromosome number (Zou et al. [1999]). Like most cancer-related genes, the expression of PTTG is restricted in normal tissues, but PTTG expression is dramatically increased in malignant human cell lines, pituitary tumors, colon carcinomas and colorectal tumors. (Zhang, X., et al. [1999a]; Zhang, X., et al., *Pituitary tumor transforming gene (PTTG) expression in pituitary adenornas*, J. Clin. Endocrinol. Metab. 84:761–767 [1999b]; Heaney, A. R., et al., *Pituitary tumor transforming gene: a novel marker in colorectal tumors*, Lancet [In Press; 2000]).

The recent discovery of a human PTTG gene 2, which shares high sequence homology with human PTTG1, implying the existence of a PTTG gene family. (Prezant, T. R., et al., *An intronless homolog of human proto-oncogene hPTTG is expressed in pituitary tumors: evidence for hPTTG family*, J. Clin Endocrinol. Metab. 84:1149–1152 [1999]). Murine PTTG shares 66% nucleotide base sequence homology with human PTTG1 and also exhibits transforming ability. (Wang, Z. and Melmed, S., *Characterization of the murine pituitary tumor transforming gone (PTTG) and its promoter*, Endocrinology [In Press; 2000]). A proline-rich region was identified near the protein C-terminus that is critical for PTTG1's transforming activity. (Zhang, X., et al. [1999a]), as demonstrated by the inhibitory effect on in vitro transformation, in vivo tumorigenesis, and transactivation, when point mutations were introduced into the proline-rich region. Proline-rich domains may function as SH3 binding sites to mediate signal transduction of protein-tyrosine kinase. (Pawson, T., *Protein modules and signaling networks*, Nature 373:573–580 [1995]; Kuriyan, J., and Cowburn, D., *Modular peptide recognition domains in eukaryotic signaling*, Annu, Rev. Biophys Biomol. Struct. 26:259–288 [1997]).

There remains a need for a therapeutic treatment for neoplasms, such as cancer, that inhibits neoplastic cellular proliferation and/or transformation associated with PTTG overexpression. This and other benefits are provided by the present invention as described herein.

SUMMARY OF THE INVENTION

The present invention relates to a method of inhibiting neoplastic cellular proliferation and/or transformation of mammalian cells, including cells of human origin, whether in vitro or in vivo. The inventive method relies on the discovery that the native carboxy-terminal portion of the pituitary tumor transforming gene protein (PTTG) is critical to PTTG protein function and that, surprisingly, pituitary tumor transforming gene carboxy-terminal peptide (PTTG-C) molecules have the ability to downregulate pituitary tumor transforming gene (PTTG) expression and/or PTTG function in a dominant negative manner. In some embodiments, the invention is directed to gene-based treatments that deliver PTTG carboxy-terminal-related polynucleotides to mammalian cells to inhibit the endogenous expression and function of PTTG. Other embodiments are directed to peptide-based treatments that deliver PTTG-C peptides to the cells, which inhibit endogenous PTTG expression and/or PTTG function.

In particular, useful gene-based embodiments of the method of inhibiting neoplastic cellular proliferation and/or transformation of mammalian cells involve delivering to the cell a composition comprising a PTTG-C-related polynucleotide that includes a base sequence that defines a PTTG carboxy-terminal peptide-encoding sequence, or defines a degenerate sequence, or defines a sequence complementary to either of these. In accordance with the method, the PTTG carboxy-terminal-related polynucleotide, preferably complexed with a cellular uptake-enhancing agent, is delivered in an amount and under conditions sufficient to enter the cell, thereby inhibiting neoplastic cellular proliferation and/or transformation of the cell.

Alternatively, useful peptide-based embodiments of the method of inhibiting neoplastic cellular proliferation and/or transformation of a mammalian cell involve delivering to a mammalian cell a composition comprising a PTTG carboxy-terminal peptide (PTTG-C), or a biologically functional fragment thereof, preferably complexed with a cellular uptake-enhancing agent, in an amount and under conditions sufficient to enter the cell, thereby inhibiting neoplastic cellular proliferation and/or transformation Because, PTTG protein further mediates the expression of bFGF, an important angiogenesis activator, the inventive method of inhibiting neoplastic cellular proliferation and/or transformation, practiced in vivo, also encompasses a method of inhibiting tumor angiogenesis. Angiogenesis activators, including bFGF and VEGF, are expressed and secreted by most human carcinoma cells. (Plate, K. H et al., Nature 359:845–48 [1992]; Schultz-Hector, S. and Haghayegh, S., Cancer Res. 53:1444–49 [1993]; Yamanaka, Y. et al., Cancer Res. 53:5289–96 [1993]; Buensing, S. et al., Anticancer Res. 15:2331–34 [1995]). The discovery, described herein, that the inventive PTTG-C peptides dramatically reduce bFGF production by cancer cells (e.g., HeLa), shows that in accordance with the inventive method, the inventive PTTG-C peptides can impair new blood vessel growth, which is essential for tumor growth. Thus, the method of inhibiting tumor angiogenesis further inhibits neoplastic cellular proliferation, in vivo.

The present invention also relates to compositions useful for inhibiting neoplastic cellular proliferation and/or transformation. These include compositions comprising a PTTG carboxy-terminal peptide or comprising a chimeric or fusion protein that contains a first PTTG carboxy-terminal peptide segment and a second cellular uptake-enhancing peptide segment. The invention also relates to compositions comprising a PTTG carboxy-terminal-related polynucleotide, for example, a polynucleotide encoding a PTTG-C peptide or antisense PTTG-C-related oligonucleotides. Also included in the invention are compositions comprising expression vectors containing the PTTG-C-related polynucleotides, including nucleic acids encoding PTTG-C peptides. The inventive PTTG-C peptides and inventive PTTG-C-related polynucleotides are useful in the manufacture of pharmaceutical compositions, medicaments or medicants for inhibiting neoplastic cellular proliferation and/or transformation, which contain the inventive PTTG-C peptides and PTTG-C-related polynucleotides.

In accordance with the present invention, there are also provided PTTG carboxy-terminal (PTTG-C) peptides and PTTG-C-related polynucleotides, which can also be isolated from other cellular components. The inventive PTTG-C peptides are useful in bioassays, as immunogens for producing anti-PTTG antibodies, or in therapeutic compositions containing such peptides and/or antibodies. Also provided are transgenic non-human mammals that comprise mammalian cells that comprise embodiments of the inventive PTTG-C-related polynucleotides and express the inventive PTTG-C peptides.

Also provided are antibodies that are specifically immunoreactive with PTTG proteins, or more particularly, with PTTG-C peptides. The inventive antibodies specifically bind to PTTG-C peptides. These anti-PTTG-C-specific antibodies are useful in assays to determine levels of PTTG proteins or PTTG-C peptides present in a given sample, e.g., tissue samples, biological fluids, Western blots, and the like. The antibodies can also be used to purify PTTG proteins or PTTG-C peptides from crude cell extracts and the like. Moreover, these antibodies are considered therapeutically useful to counteract or supplement the biological effect of PTTG proteins in vivo.

The present invention is further described by related applications U.S. Ser. No. 09/569,956, filed May 12, 2000, U.S. Ser. No. 08/894,251, filed Jul. 23, 1999, international application PCT/US97/21463, filed Nov. 21, 1997, and U.S. provisional application No. 60/031,338, filed Nov. 21, 1996, the disclosures and drawings of which are incorporated by reference.

BRIEF DESCRIPTION OF THE DRAWINGS

FIG. 2 shows PTTG-C and PTTG-Cpm expression in transfected tumor cells.

DESCRIPTION OF THE PREFERRED EMBODIMENTS OF THE INVENTION

Figure 1:
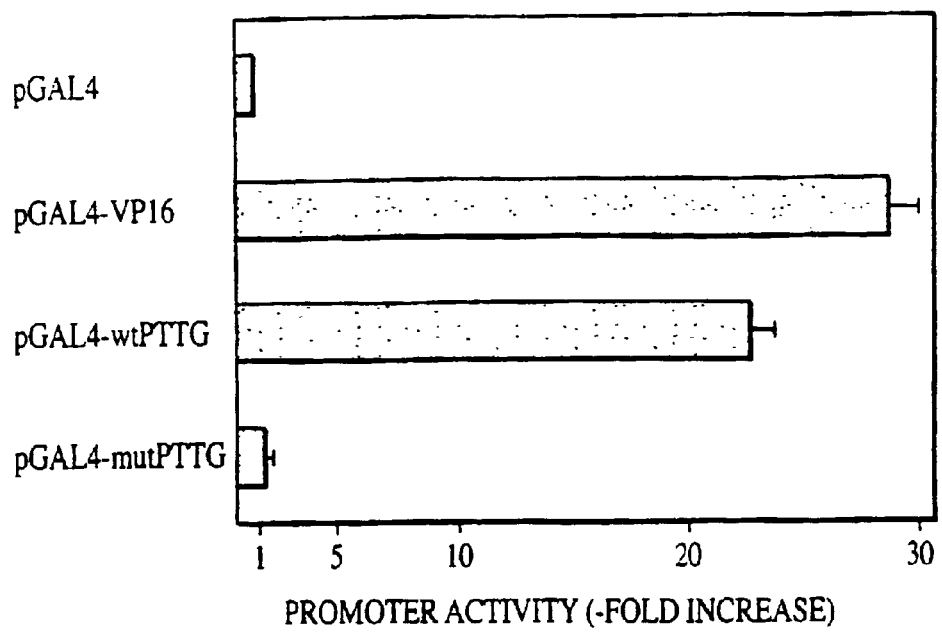
FIG. 1 illustrates transcriptional activation in transfected NIH 3T3 cells, as mediated by pGAL4, pGAL4-VP16, pGAL4-wtPTTG, or pGAL4-mutPTTG 48 hours after transfection. Cell lysate proteins were assayed for luciferase and β-gal expression pGAL4 was used as a negative control and pGAL4-VP16 as a positive control.

The present invention relates to a method of inhibiting PTTG-mediated neoplastic cellular proliferation and/or transformation of a mammalian cell, including but not limited to, a cell of human or non-human origin. Non-human mammalian cells also originate from, or in, any mammalian animal, e.g., a non-human primate, rat, mouse, rabbit, guinea pig, hamster, bovine, porcine, ovine, equine, canine, feline, pachyderm, and the like. The mammalian cell can be situated in vivo, i.e., within a mammalian animal subject or human subject, or in vitro, i.e., the cell can be a cultured cell.

For the purposes of the invention, "neoplastic cellular proliferation" includes neoplastic (malignant or benign), hyperplastic, cytologically dysplastic and/or premalignant cellular growth or proliferation in a mammalian subject or cell culture. Hyperplastic cellular growth or proliferation includes abnormal multiplication or increase in the numbers of normal cells in a normal arrangement in a tissue, for example, as is common in benign prostatic hyperplasia. Cytologically dysplastic and/or premalignant cellular growth or proliferation include increases in cellular numbers of karyotypically abnormal but non-malignant cells within a tissue. Examples include some benign prostatic hyperplasias/dysplasia and cervical hyperplasias/dysplasias.

Neoplastic cellular growth and/or proliferation, i.e., growth of abnormally organized tissue, includes malignant and non-malignant neoplasms. Malignant neoplasms include primary, recurrent, and/or or metastatic cancerous tumors originating in any tissues, for example, carcinomas, sarcomas, lymphomas, mesotheliomas, melanomas, gliomas, nephroblastomas, glioblastomas, oligodendrogliomas, astrocytomas, ependymomas, primitive neuroectodermal tumors, atypical meningiomas, malignant meningiomas, or neuroblastomas, originating in the pituitary, hypothalamus, lung, kidney, adrenal, ureter, bladder, urethra, breast, prostate, testis, skull, brain, spine, thorax, peritoneum, ovary, uterus, stomach, liver, bowel, colon, rectum, bone, lymphatic system, skin, or in any other organ or tissue of the subject.

In accordance with gene-based embodiments of the method of inhibiting neoplastic cellular proliferation and/or transformation, an inventive composition is delivered to the cell, which composition comprises a PTTG carboxy-terminal-related polynucleotide. A "PTTG carboxyterminal-related" polynucleotide is a polynucleotide having a contiguous sequence of bases (e.g., adenine [A], thymine [T], uracil [U], guanine [G], and/or cytosine [C]) defining a sequence specific to the 3' coding region of PTTG. The 3'-end or terminal extends from approximately the mid-point of a cDNA coding sequence encoding a native PTTG to its end at a stop codon.

The PTTG carboxy-terminal-related polynucleotide can be a sequence encoding a carboxy-terminal portion of a mammalian PTTG protein (i.e., a PTTG-C peptide), as described more fully below, or encoding a PTTG-specific fragment thereof, or a degenerate coding sequence, or a sequence complementary to any of these.

In some preferred embodiments, the inventive composition includes a nucleic acid construct, such as a plasmid or viral expression vector, which comprises the polynucleotide in a sense or antisense orientation, and from which PTTG-specific mRNA transcript can be expressed in the cell. In a preferred embodiment, the nucleic acid construct contains a polynucleotide encoding a mammalian PTTG carboxy-terminal (PTTG-C) peptide, which can be any PTTG-C peptide or functional fragment thereof as described herein. The composition can also contain one or more helper plasmids or viruses, if appropriate. The plasmid or viral expression vector is a nucleic acid construct that includes a promoter region operatively linked to the polynucleotide in a transcriptional unit.

As used herein, a promoter region refers to a segment of DNA that controls transcription of a DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

As used herein, the term "operatively linked" refers to the functional relationship of DNA with regulatory and effect or nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. Thus, "operatively linked" means that, within a transcriptional unit, the promoter sequence, is located upstream (i.e., 5' in relation thereto) from the coding sequence and the coding sequence, is 3' to the promoter, or alternatively is in a sequence of genes or open reading frames 3' to the promoter and expression is coordinately regulated thereby. Both the promoter and coding sequences are oriented in a 5' to 3' manner, such that transcription can take place in vitro in the presence of all essential enzymes, transcription factors, co-factors, activators, and reactants, under favorable physical conditions, e.g., suitable pH and temperature. This does not mean that, in any particular cell, conditions will favor transcription. For example, transcription from a tissue-specific promoter is generally not favored in heterologous cell types from different tissues.

The term "nucleic acid" encompasses ribonucleic acid (RNA) or deoxyribonucleic acid (DNA), which DNA can be complementary DNA (cDNA) or genomic DNA, e.g. a gene encoding a PTTG protein. "Polynucleotides" encompass nucleic acids containing a "backbone" formed by phosphodiester linkages between ribosyl or deoxyribosyl moieties. Polynucleotides also include nucleic acid analogs, for example polynucleotides having alternative linkages as known in the art. Examples include phosphorothioate linkages (e.g., phosphorothioate oligodeoxynucleotides; S-oligonucleotides), mixed phosphorothioate and phosphodiester linkages (e.g., S—O-oligodeoxynucleotides and phosphodiester/phosphorothioate 2'-O-methyl-oligoribonucleotides; Zhou, W. et al., *Mixed backbone oligonucleotides as second-generation antisense agents with reduced phosphthioate-related side effects*, Bioorg. Med Chem. Lett. 8(22):3269–74 [1998]), methylphosphonate-phosphodiester modifications (MP—O-oligonucleotides; Zhao, Q. et al., *Comparison of cellular binding and uptake of antisense phosphodiester, phosphorothioate, and mixed phosphorothioate and methylphosphonate oligonucleotides*, Antisense Res. Dev. 3(1):53–66 [1993]), or morpholino oligonucleotides (e.g., Schmajuk, G. et al., *Antisense oligonucleotides with different backbones. Modification of splicing pathways and efficacy of uptake*, J. Biol. Chem. 274(31) :21783–89 [1999]).

Also included among useful polynucleotides are nucleic acid analogs having a pseudopeptide or polyamide backbone comprising N-(2-aminoethyl)glycine moieties, i.e., peptide nucleic acids (PNA). (E.g., Nielsen, P. E., *Peptide nucleic acids: on the road to new gene therapeutic drugs*, Pharmacol. Toxicol. 86(1):3–7 [2000]; Soomets, U. et al., *Antisense properties of peptide nucleic acids*, Front. Biosci. 4:D782–86 [1999]; Tyler, B. M. et al., *Peptide nucleic acids targeted to the neurotensin receptor and administered i.p. cross the blood-brain barrier and specifically reduce gene expression*, Proc. Natl. Acad. Sci. USA 96(12):7053–58 [1999]).

Polynucleotides include sense or antisense polynucleotides. "Polynucleotides" also encompasses "oligonucleotides".

A polynucleotide sequence complementary to a PTTG-specific polynucleotide sequence, as used herein, is one binding specifically with a PTTG-specific nucleotide base sequence. The phrase "binding specifically" encompasses the ability of a polynucleotide sequence to recognize a complementary base sequence and to form double-helical segments therewith via the formation of hydrogen bonds between the complementary base pairs. Thus, a complementary sequence includes, for example, an antisense sequence with respect to a sense sequence or coding sequence.

In some embodiments of the PTTG-C-related polynucleotide, the polynucleotide is in a sense orientation within the transcriptional unit, such that mRNA transcript can be produced, which when translated results in a translation product, such as a PTTG protein or a PTTG carboxy-terminal peptide (PTTG-C). In other embodiments, the PTTG-C-related polynucleotide is in an antisense orientation such that transcription results in a transcript complementary to and hybridizable with a naturally-occurring sense PTTG mRNA molecule under physiological conditions, inhibiting or blocking translation therefrom. Thus, antisense oligonucleotides inactivate target mRNA sequences by either binding thereto and inducing degradation of the mRNA by, for example, RNase I digestion, or inhibiting translation of mRNA target sequence by interfering with the binding of translation-regulating factors or ribosomes, or by inclusion of other chemical structures, such as ribozyme sequences or reactive chemical groups which either degrade or chemically modify the target mRNA. For example, an antisense oligonucleotide targeted to a PTTG carboxy-terminal-related polynucleotide segment of mRNA or genomic DNA is effective in inhibiting expression of PTTG.

Gene-based therapy strategies employing antisense oligonucleotides are well known in the art. (E.g., Rait, A. et al., *3'-End conjugates of minimally phosphorothioate-protected oligonucleotides with 1-O-hexadecylglycerol: synthesis and anti-ras activity in radiation-resistant cells*, Bioconjug Chem., 11(2):153–60 [2000]; Stenton, G. R. et al., *Aerosolized syk antisense suppresses syk expression, mediator release from macrophages, and pulmonary inflammation*, J. Immunol., 164(7):3790–7 [2000]; Suzuki, J. et al., *Antisense Bcl-x oligonucleotide induces apoptosis and prevents arterial neointimal formation in murine cardiac allografts*, Cardiovas. Res., 45(3):783–7 [2000]; Kim, J. W. et al., *Antisense oligodeoxynucleotide of glyceraldehyde-3-phosphate dehyrdogenase gene inhibits cell proliferation and induces apoptosis in human cervical carcinoma cell line*, Antisense Nucleic Acid Drug Dev., 9(6):507–13 [1999]; Han, D. C. et al., *Therapy with antisense TGF-beta1 oligodeoxynucleotides reduces kidney weight and matrix mRNAs in diabetic mice*, Am. J. Physiol. Renal Physiol., 278(4):F628-F634 [2000]; Scala, S. et al., *Adenovirus-mediated suppression of HMGI (Y) protein synthesis as potential therapy of human malignant neoplasias*, Proc. Natl. Acad. Sci. USA., 97(8):4256–4261 [2000]; Arteaga, C. L., et al., *Tissue-targeted antisense c-fos retroviral vector inhibits established breast cancer xenografts in nude mice*, Cancer Res., 56(5):1098–1103 [1996]; Muller, M. et al., *Antisense phosphorothioate oligodeoxynucleotide down-regulation of the insulin-like growth factor I receptor in ovarian cancer cells*, Int. J. Cancer, 77(4):567–71 [1998]; Engelhard, H. H., *Antisense Oligodeoxynucleotide Technology: Potential Use for the Treatment of Malignant Brain Tumors*, Cancer Control, 5(2):163-170 [1998]; Alvarez-Salas, L. M. et al., *Growth inhibition of cervical tumor cells by antisense oligodeoxynucleotides directed to the human papillomavirus type 16 E6 gene*, Antisense Nucleic Acid Drug Dev., 9(5):441–50 [1999]; Im, S. A., et al., *Antiangiogenesis treatment for gliomas: transfer of antisense-vascular endothelial growth factor inhibits tumor growth in vivo*, Cancer Res., 59(4):895–900 [1999]; Maeshima, Y. et al., *Antisense oligonucleotides to proliferating cell nuclear antigen and Ki-67 inhibit human mesangial cell proliferation*, J. Am. Soc. Nephrol., 7(10):2219–29 [1996]; Chen, D S. et al., *Retroviral Vector-mediated transfer of an antisense cyclin G1 construct inhibits osteosarcoma tumor growth in nude mice*, Hum. Gene Ther, 8(14):1667–74 [1997]; Hirao, T. et al., *Antisense epidermal growth factor receptor delivered by adenoviral vector blocks tumor growth in human gastric cancer*, Cancer Gene Ther. 6(5):423–7 [1999]; Wang, X. Y. et al., *Antisense inhibition of protein kinase Calpha reverses the transformed phenotype in human lung carcinoma cells*, Exp. Cell Res., 250(1):253–63 [1999]; Sacco, M G. et al., *In vitro and in vivo antisense-mediated growth inhibition of a mammary adenocarcinoma from MMTV-neu transgenic mice*, Gene Ther., 5(3);388–93 [1998]; Leonetti, C. et al., *Antitumor effect of c-myc antisense phosphorothioate oligodeoxynucleotides on human melanoma cells in vitro and in mice*, J. Natl. Cancer Inst., 88(7):419–29 [1996]; Laird, A. D. et al., *Inhibition of tumor growth in liver epthelial cells transfected with a transforming growth factor alpha antisense gene*, Cancer Res. 54(15): 4224–32 (Aug. 1, 1994); Yazaki, T. et al., *Treatment of glioblastoma U-87 by systemic administration of an antisense protein kinase C-alpha phosphorothioate oligodeoxynucleotide*, Mol. Pharmacol., 50(2):236–42 [1996]; Ho, P. T. et al., *Antisense oligonucleotides as therapeutics for malignant diseases*, Semin. Oncol, 24(2): 187–202 [1997]; Muller, M. et al., *Antisense phosphorothioate oligodeoxynucleotide down-regulation of the insulin-like growth factor I receptor in ovarian cancer cells*, Int. J. Cancer, 77(4):567–71 [1998]; Elez, R. et al., *Polo-like kinase1, a new target for antisense tumor therapy*, Biochem. Biophys. Res. Commun., 269(2):352–6 [2000]; Monia, B. P. et al., *Antitumor activity of a phosphorothioate antisense oligodeoxynucleotide targeted against C-raf kinase*, Nat. Med., 2(6):668–75 [1996]).

In other embodiments of the inventive method, the inventive composition comprises a PTTG carboxy-terminal-related polynucleotide that is not contained in an expression vector, for example, a synthetic antisense oligonucleotide, such as a phosphorothioate oligodeoxynucleotide. Synthetic antisense oligonucleotides, or other antisense chemical structures designed to recognize and selectively bind to mRNA, are constructed to be complementary to portions of the PTTG coding strand, for example, to coding sequences shown in SEQ ID NOS: 1, 3, 10, 15, 18, or 19 (Tables 1–6 below). By preventing translational expression of at least part of the PTTG 3' coding region, an antisense PTTG carboxy-terminal-related polynucleotide is useful, in accordance with the inventive method, to prevent expression of PTTG protein that is functional in mediating neoplastic cellular proliferation and/or transformation.

In preferred embodiments of the method of inhibiting neoplastic cellular proliferation and/or transformation, the composition also comprises an uptake-enhancing agent as further described herein. Inventive compositions, containing the uptake-enhancing agent complexed with a PTTG-specific polynucleotide, are designed to be capable of passing through the cell membrane in order to enter the cytoplasm of the cell by virtue of physical and chemical properties. In addition, the composition can be designed for delivery only to certain selected cell populations by targeting the composition to be recognized by specific cellular uptake mechanisms which take up the PTTG-specific polynucleotides only within select cell populations. For example, the composition can include a receptor agonist to bind to a receptor found only in a certain cell type.

The inventive composition can also optionally contain one or more pharmaceutically acceptable carrier(s). As used herein, the term "acceptable carrier" encompasses any of the standard pharmaceutical carriers. The carrier can be an organic or inorganic carrier or excipient, such as water and emulsions such as an oil/water or water/oil emulsion, and various types of wetting agents. The active ingredient(s) can optionally be compounded in a composition formulated, for example, with non-toxic, pharmaceutically acceptable carriers for infusions, tablets, pellets, capsules, solutions, emulsions, suspensions, and any other form suitable for use.

Such carriers also include glucose, lactose, gum acacia, gelatin, mannitol, starch paste, magnesium trisilicate, talc, corn starch, keratin, colloidal silica, potato starch, urea, medium chain length triglycerides, dextrans, normal saline, phosphate buffered saline and other carriers suitable for use in manufacturing preparations, in solid, semisolid, or liquid form. In addition auxiliary, stabilizing, thickening and coloring agents and perfumes can be used as appropriate.

PTTG-specific polynucleotides, including PTTG carboxy-terminal-related polynucleotides, are determined by base sequence similarity or homology to known mammalian PTTG-specific nucleotide sequences. Base sequence homology is determined by conducting a base sequence similarity search of a genomics data base, such as the GenBank database of the National Center for Biotechnology Information (NCBI; www.ncbi nlm nih gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data). (E.g., Altchul, S. F., et al., *Gapped BLAST and PSI-BLAST: a new generation of protein database search programs*, Nucleic Acids Res. 25(17):3389–402 [1997]; Zhang, J., & Madden, T. L., *PowerBLAST: a new network BLAST application for interactive or automated sequence analysis and annotation*, Genome Res. 7(6):649–56 [1997]; Madden, T. L., et al., *Applications of network BLAST server*, Methods Enzymol. 266:131–41 [1996], Altschul, S. F., et al., *Basic local alignment search tool*, J. Mol. Biol. 215(3):403–10 [1990]) Preferably, a PTTG-specific polynucleotide sequence is at least 5 to 30 contiguous nucleotides long, more preferably at least 6 to 15 contiguous nucleotides long, and most preferably at least 7 to 10 contiguous nucleotides long. Preferably, the inventive PTTG carboxy-terminal-related polynucleotide is at least about 45 contiguous nucleotides long.

Preferred examples of PTTG-specific coding sequences include the sequence for human PTTG (hPTTG or PTTG1). The PTTG1 peptide is encoded by the open reading frame at nucleotide positions 95 through 700 of human PTTG1 gene sequence SEQ. ID. NO.: 3 (Table 1 below).

TABLE 1

PTTG1 gene sequence.

|  |  |  |  |  |  |  |
|---|---|---|---|---|---|---|
| 1 | ATGGCCGCGA | GTTGTGGTTT | AAACCAGGAG | TGCCGCGCGT | CCGTTCACCG | (SEQ. ID. NO.:3) |
| 51 | CGGCCTCAGA | TGAATGCGGC | TGTTAAGACC | TGCAATAATC | CAGAATGGCT |  |
| 101 | ACTCTGATCT | ATGTTGATAA | GGAAAATGGA | GAACCAGGCA | CCCGTGTGGT |  |
| 151 | TGCTAAGGAT | GGGCTGAAGC | TGGGGTCTGG | ACCTTCAATC | AAAGCCTTAG |  |
| 201 | ATGGAGATC | TCAAGTTTCA | ACACCACGTT | TTGGCAAAAC | GTTCGATGCC |  |
| 251 | CCACCAGCCT | TACCTAAAGC | TACTAGAAAG | GCTTTGGGAA | CTGTCAACAG |  |
| 301 | AGCTACAGAA | AAGTCTGTAA | AGACCAAGGG | ACCCCTCAAA | CAAAAACAGC |  |
| 351 | CAAGCTTTTC | TGCCAAAAAG | ATGACTGAGA | AGACTGTTAA | AGCAAAAAGC |  |
| 401 | TCTGTTCCTG | CCTCAGATGA | TGCCTATCCA | GAAATAGAAA | AATTCTTTCC |  |
| 451 | CTTCAATCCT | CTAGACTTTG | AGAGTTTTGA | CCTGCCTGAA | GAGCACCAGA |  |
| 501 | TTGCGCACCT | CCCCTTGAGT | GGAGTGCCTC | TCATGATCCT | TGACGAGGAG |  |
| 551 | AGAGAGCTTG | AAAAGCTGTT | TCAGCTGGGC | CCCCCTTCAC | CTGTGAAGAT |  |
| 601 | GCCCTCTCCA | CCATGGGAAT | CCAATCTGTT | GCAGTCTCCT | TCAAGCATTC |  |
| 651 | TGTCGACCCT | GGATGTTGAA | TTGCCACCTG | TTTGCTGTGA | CATAGATATT |  |
| 701 | TAAATTTCTT | AGTGCTTCAG | AGTTTGTGTG | TATTTGTATT | AATAAAGCAT |  |
| 751 | TCTTTAACAG | ATAAAAAAAA | AAAAAAAA. |  |  |  |

The 3' coding region of PTTG1 includes the following 168-nucleotide sequence, which corresponds to nucleotide positions 533 through 700 of SEQ. ID. NO.: 3, shown in Table 2 below.

TABLE 2

Portion of 3' coding region of PTTG1

|  |  |  |  |  |  |
|---|---|---|---|---|---|
| 1 | ATGATCCTTG | ACGAGGAGAG | AGAGCTTGAA | AAGCTGTTTC | AGCTGGGCCC | (SEQ.ID. NO.:10) |
| 51 | CCCTTCACCT | GTGAAGATGC | CCTCTCCACC | ATGGGAATCC | AATCTGTTGC |  |
| 101 | AGTCTCCTTC | AAGCATTCTG | TCGACCCTGG | ATGTTGAATT | GCCACCTGTT |  |
| 151 | TGCTGTGACA | TAGATATT. |  |  |  |  |

Another useful example of a PTTG-specific coding sequence is a sequence that encodes a rat PTTG peptide, including nucleotide positions 293 through 889 of SEQ. ID. NO.: 1 (Table 3 below).

TABLE 3

Rat PTTG sequence.

| | |
|---|---|
| AATTCGGCAC GAGCCAACCT TGAGCATCTG ATCCTCTTGG CTTCTCCTTC CTATCGCTGA | 60 (SEQ. ID. NO.:1) |
| GCTGGTAGGC TGGAGACAGT TGTTTGGGTG CCAACATCAA CAAACGATTT CTGTAGTTTA | 120 |
| GCGTTTATGA CCCTGGCGTG AAGATTTAAG GTCTGGATTA AGCCTGTTGA CTTCTCCAGC | 180 |
| TACTTCTAAA TTTTTGTGCA TAGGTGCTCT GGTCTCTGTT GCTGCTTAGT TCTTCCAGCC | 240 |
| TTCCTCAATG CCAGTTTTAT AATATGCAGG TCTCTCCCCT CAGTAATCCA GG ATG | 295 |
| GCT ACT CTG ATC TTT GTT GAT AAG GAT AAC GAA GAG CCA GGC AGC CGT | 343 |
| TTG GCA TCT AAG GAT GGA TTG AAG CTG GGC TCT GGT GTC AAA GCC TTA | 391 |
| GAT GGG AAA TTG CAG GTT TCA ACG CCA CGA GTC GGC AAA GTG TTC GGT | 439 |
| GCC CCA GGC TTG CCT AAA GCC AGC AGG AAG GCT CTG GGA ACT GTC AAC | 487 |
| AGA GTT ACT GAA AAG CCA GTG AAG AGT AGT AAA CCC CTG CAA TCG AAA | 535 |
| CAG CCG ACT CTG AGT GTG AAA AAG ATC ACC GAG AAG TCT ACT AAG ACA | 583 |
| CAA GGC TCT GCT CCT GCT CCT GAT GAT GCC TAC CCA GAA ATA GAA AAG | 631 |
| TTC TTC CCC TTC GAT CCT CTA GAT TTT GAG AGT TTT GAC CTG CCT GAA | 679 |
| GAG CAC CAG ATC TCA CTT CTC CCC TTG AAT GGA GTG CCT CTC ATG ATC | 727 |
| CTG AAT GAA GAG AGG GGG CTT GAG AAG CTG CTG CAC CTG GAC CCC CCT | 775 |
| TCC CCT CTG CAG AAG CCC TTC CTA CCG TGG GAA TCT GAT CCG TTG CCG | 823 |
| TCT CCT CCC AGC GCC CTC TCC GCT CTG GAT GTT GAA TTG CCG CCT GTT | 871 |
| TGT TAC GAT GCA GAT ATT TAAACGTCTT ACTCCTTTAT AGTTTATGTA | 919 |
| AGTTGTATTA ATAAAGCATT TGTGTGTAAA AAAAAAAAA AAAACTCGAG AGTAC | 974 |

The 3' coding region of rat PTTG includes the following 168-nucleotide sequence, which corresponds to nucleotide positions 722 through 889 of SEQ. ID. NO.: 1, shown in Table 4 below.

TABLE 4

Portion of 3' coding region of rat PTTG.

| | |
|---|---|
| ATG ATC CTG AAT GAA GAG AGG GGG CTT GAG AAG CTG CTG CAC CTG GAC | 48 (SEQ. ID. NO.:18) |
| CCC CCT TCC CCT CTG CAG AAG CCC TTC CTA CCG TGG GAA TCT GAT CCG | 96 |
| TTG CCG TCT CCT CCC AGC GCC CTC TCC GCT CTG GAT GTT GAA TTG CCG | 144 |
| CCT GTT TGT TAC GAT GCA GAT ATT. | 168 |

Another useful example of a PTTG-specific coding sequence is a sequence that encodes a murine PTTG peptide, including nucleotide positions 304 through 891 of SEQ. ID. NO.: 15 (Table 5 below).

As used herein, the term "degenerate" refers to codons that differ in at least one nucleotide from a reference nucleic acid, e.g., SEQ ID NOS: 1, 3, 10, 15, 18, or 19, but encode the same amino acids as the reference nucleic acid. For

TABLE 5

Murine PTTG sequence.

```
  1 TCTTGAACTT GTTATGTAGC AGGAGGCCAA ATTTGAGCAT CCTCTTGGCT TCTCTTTATA  (SEQ. ID. NO.:15)

61 GCAGAGATTG TAGGCTGGAG ACAGTTTTGA TGGGTGCCAA CATAAACTGA TTTCTGTAAG

121 AGTTGAGTGT TTTATGACCC TGGCGTGCAG ATTTAGGATC TGGATTAAGC CTGTTGACTT

181 CTCCAGCTAC TTATAAATTT TTGTGCATAG GTGCCCTGGG TAAAGCTTGG TCTCTGTTAC

241 TGCGTAGTTT TTCCAGCCGT CTCAATGCCA ATATTCAGGC TCTCTCCCTT AGAGTAATCC

301 AGAATGGCTA CTCTTATCTT TGTTGATAAG GATAATGAAG AACCCGGCCG CCGTTTGGCA

361 TCTAAGGATG GGTTGAAGCT GGGCACTGGT GTCAAGGCCT TAGATGGGAA ATTGCAGGTT

421 TCAACGCCTC GAGTCGGCAA AGTGTTCAAT GCTCCAGCCG TGCCTAAAGC CAGCAGAAAG

481 GCTTTGGGGA CAGTCAACAG AGTTGCCGAA AAGCCTATGA AGACTGGCAA ACCCCTCCAA

541 CCAAAACAGC CGACCTTGAC TGGGAAAAAG ATCACCGAGA AGTCTACTAA GACACAAAGC

601 TCTGTTCCTG CTCCTGATGA TGCCTACCCA GAAATAGAAA AGTTCTTCCC TTTCAATCCT

661 CTAGATTTTG ACCTGCCTGA GGAGCACCAG ATCTCACTTC TCCCCTTGAA TGGCGTGCCT

721 CTCATCACCC TGAATGAAGA GAGAGGGCTG GAGAAGCTGC TGCATCTGGG CCCCCCTAGC

781 CCTCTGAAGA CACCCTTTCT ATCATGGGAA TCTGATCCGC TGTACTCTCC TCCCAGTGCC

841 CTCTCCACTC TGGATGTTGA ATTGCCGCCT GTTTGTTACG ATGCAGATAT TTAAACTTCT

901 TACTTCTTTG TAGTTTCTGT ATGTATGTTG TATTAATAAA GCATT.
```

The 3' coding region of murine PTTG includes the following 168-nucleotide sequence, which corresponds to nucleotide positions 724 through 891 of SEQ. ID. NO.: 15, shown in Table 6 below.

example, codons specified by the triplets "UCU", "UCC", "UCA", and "UCG" are degenerate with respect to each other since all four of these codons encode the amino acid serine.

TABLE 6

Portion of 3' coding region of murine PTTG.

```
ATCACCCTGA ATGAAGAGAG AGGGCTGGAG AAGCTGCTGC ATCTGGGCCC CCCTAGCCCT   60 (SEQ. ID. NO.:19)

CTGAAGACAC CCTTTCTATC ATGGGAATCT GATCCGCTGT ACTCTCCTCC CAGTGCCCTC  120

TCCACTCTGG ATGTTGAATT GCCGCCTGTT TGTTACGATG CAGATATT.                168
```

Inventive PTTG-C-related polynucleotides having nucleotides sequences of SEQ. ID. NOS.: 10, 18, or 19, degenerate coding sequences, or sequences complementary to any of these, are merely illustrative of useful PTTG carboxy-terminal-related polynucleotides. Other useful PTTG carboxy-terminal-related polynucleotides are functional fragments of any of SEQ. ID. NOS.: 10, 18, or 19 at least about 45 contiguous nucleotides long, degenerate coding sequences, or sequences complementary to any of these, the presence of which in the cell can function to downregulate endogenous PTTG expression and/or PTTG function, which functionality can be determined by routine screening.

Other useful polynucleotides include nucleic acids or other polynucleotides, that differ in sequence from the sequences shown in SEQ ID NO.:1, SEQ. ID. NO.:3, SEQ. ID. NO.:10, SEQ. ID. NO.:15, SEQ. ID. NO.:18, and SEQ. ID. NO.:19, but which when expressed in a cell, result in the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner, compared to any of the detailed nucleotide sequences disclosed herein, to produce PTTG protein functional with respect to inducing neoplastic cellular proliferation and/or transformation, or PTTG-C peptide(s) functional with respect to inhibition of neoplastic cellular proliferation and/or transformation, and/or polypeptide products functional with respect to immunogenicity. Such polynucleotides can have substantially the same coding sequences as the reference sequences, encoding the amino acid sequence as set forth in SEQ. ID. NO.:2, SEQ. ID. NO.:4, SEQ. ID. NO.:9, SEQ. ID. NO:14, SEQ. ID. NO.:16, or SEQ. ID. NO.:17 or a larger amino acid sequence including SEQ. ID. NO.:2, SEQ. ID. NO.:4, SEQ. ID. NO.:9, SEQ. ID. NO.:14, SEQ. ID. NO.:16, or SEQ. ID. NO.:17. As employed herein, the term "substantially the same nucleotide sequence" refers to DNA having sufficient identity to the reference polynucleotide, such that it will hybridize to the reference nucleotide under moderately stringent hybridization conditions. In other embodiments, DNA having "substantially the same nucleotide sequence" as the reference nucleotide sequence has at least about 60% identity with respect to the reference nucleotide sequence. DNA having at least 70%, more preferably at least 90%, yet more preferably at least 95%, identity to the reference nucleotide sequence is preferred.

In preferred embodiments, functionally equivalent nucleic acids encode polypeptides or peptide fragments that are the same as those disclosed herein or that have conservative amino acid variations, or that encode larger polypeptides that include SEQ. ID. NO.:2, SEQ. ID. NO.:4, SEQ. ID. NO.:9, or SEQ. ID. NO.:14, SEQ. ID. NO.:16, or SEQ. ID. NO.:17, or fragments of any of these that are biologically functional fragments with respect to inhibiting neoplastic cellular proliferation and/or transformation. For example, conservative variations include substitution of a non-polar residue with another non-polar residue, or substitution of a charged residue with a similarly charged residue. These variations include those recognized by skilled artisans as those that do not substantially alter the tertiary structure of the protein.

Useful polynucleotides can be produced by a variety of methods well-known in the art, e.g., by employing PCR and other similar amplification techniques, using oligonucleotide primers specific to various regions of SEQ ID NOS:1, 3, 10, 15, 18, 19, or functionally equivalent polynucleotide sequences. Other synthetic methods for producing polynucleotides or oligonucleotides of various lengths are also well known.

In accordance with the method, preferred polynucleotides hybridize under moderately stringent, preferably high stringency, conditions to substantially the entire sequence, or substantial portions (i.e., typically at least 15–30 nucleotide) of the nucleic acid sequence set forth in SEQ ID NOS:1, 3, 10, 15, 18, or 19, or to complementary sequences.

The phrase "stringent hybridization" is used herein to refer to conditions under which annealed hybrids, or at least partially annealed hybrids, of polynucleic acids or other polynucleotides are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of relatively low stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% sequence identity or homology, preferably about 75% identity, more preferably about 85% identity to the target DNA; with greater than about 90% identity to target-DNA being especially preferred. Preferably, moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018 M NaCl at 65° C. (i.e., if a hybrid is not stable in 0.018 M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 42° C., followed by washing in 1×SSPE, 0.2% SDS, at 50° C. Denhart's solution and SSPE (see, e.g., Sambrook et al., *Molecular Cloning, A Laboratory Manual*, Cold Spring Harbor Laboratory Press [1989]) are well known to those of skill in the art as are other suitable hybridization buffers.

The PTTG carboxy-terminal-related polynucleotide can be, but is not necessarily, of homologous origin with respect to the cell, due to the relatively high degree of sequence homology among mammalian PTTG sequences. PTTG carboxy-terminal-related polynucleotides of heterologous mammalian origin with respect to the cell is also useful. Thus, for example, in accordance with the inventive method, a human PTTG-C-encoding sequence functions to down regulate endogenous PTTG expression and/or PTTG function in cells of non-human mammalian origin, such as murine or rat cells, and vice versa.

In preferred embodiments of the method of inhibiting neoplastic cellular proliferation and/or transformation of a mammalian cell, the polynucleotide is complexed with a cellular uptake-enhancing agent, in an amount and under conditions sufficient to enter the cell. An "uptake-enhancing" agent, as utilized herein, means a composition of matter for enhancing the uptake of exogenous polynucleotides, such as DNA segment(s), nucleic acid analogs, or nucleic acid constructs, into a eukaryotic cell, preferably a mammalian cell, and more preferably a human cell. The enhancement is measured relative to the polynucleotide uptake in the absence of the uptake-enhancing agent, in the process of transfecting or transducing the cell. Complexation with uptake-enhancing agent(s) generally augments the uptake of a polynucleotide into the cell and/or reduces its breakdown by nucleases during its passage through the cytoplasm.

In accordance with preferred embodiments of the inventive method, PTTG carboxy-terminal-related polynucleotides or PTTG-C peptides are complexed with an uptake-enhancing agent. "Complexed" means that the polynucleotide or peptide is a constituent or member of a complex, mixture, or adduct resulting from chemical binding or bonding between and/or among the other constituents, including the cellular uptake-enhancing agent(s), and/or their moieties. Chemical binding or bonding can have the nature of a covalent bond, ionic bond, hydrogen bond, hydrophobic bond, or any combination of these bonding types linking the constituents of the complex at any of their parts or moieties, of which a constituent can have one or a multiplicity of moieties of various sorts. Not every constituent of a complex need be bound to every other constituent, but each constituent has at least one chemical bond with at least one other constituent of the complex. Constituents can include, but are not limited to, molecular compounds of a polar, non-polar, or detergent character; ions, including cations, such as, but not limited to, $Na^+$, $K^+$, $Li^+$, $Ca^{2+}$, $Mg^{2+}$, $Fe^{2+}$, $Fe^{3+}$, $Zn^{2+}$, $Cu^+$, $Cu^{2+}$, and/or $NH_4^+$, or anions, such as, but not limited to $Cl^-$, $Br^-$, $FI^-$, $NO_3^-$, $NO_2^-$, $NO^-$, $HCO_3^-$, $CO_3^{2-}$, $SO_4^{2-}$, and/or $PO_4^{3-}$; biological molecules, such as proteins, oligopeptides, polypeptides, oligonucleotides, nucleic acids, nucleic acid constructs, plasmids, viral particles; an/or organic polymers and co-polymers.

PTTG carboxy-terminal-related polynucleotides or PTTG-C peptides can be, but are not necessarily, directly bound to the cellular uptake-enhancing agent. For example, the polynucleotide can be contained in an expression vector or other nucleic acid construct, which vector or other construct is bound to the uptake-enhancing agent at some moiety or part of he vector or construct not directly linked to the PTTG carboxy-terminal-related polynucleotide; for purposes of the present invention, the PTTG carboxy-terminal-related polynucleotide is still "complexed" with the uptake-enhancing agent, although not being directly bound to the uptake-enhancing agent by a chemical bond. As long as the polynucleotide and the uptake enhancing agent are both constituents or members of the same complex, an indirect chemical linkage suffices. An example with respect to PTTG-C peptides, is an intervening third peptide sequence linking a first PTTG-C peptide segment with a second cell uptake-enhancing and/or importation-competent peptide segment. The first and second peptide segments, indirectly linked, are "complexed" for purposes of the invention.

Examples of uptake-enhancing agents usefully complexed with the polynucleotide include cationic or polycationic lipid-DNA or liposome-DNA complexes ("lipoplexes"). Such lipoplexes can, optionally, also be coated with serum albumin or formulated as large-sized colloidally unstable complexes to further enhance transfection efficiency; the presence of calcium di-cations ($Ca^{2+}$) can also enhance lipid-based transfection efficiency. (E.g., Simoes, S. et al., *Human serum albumin enhances DNA transfection by lipoplexes and confers resistance to inhibition by serum*, Biochim. Biophys. Acta 1463(2):459–69 [2000]; Turek, J. et al., *Formulations which increase the size of lipoplexes prevent serum-associated inhibition of transfection*, J. Gene Med. 2(1):32–40 [2000]; Zudam, N. J. et al., *Lamellarity of cationic liposomes and mode of preparation of lipoplexes affect transfection efficiency*, Biochim. Biophys. Acta 1419(2):207–20 [1999]; Lam, A. M. and Cullis, P. R., *Calcium enhances the transfection potency of plasmid DNA-cationic liposome complexes*, Biochim. Biophys. Acta 1463(2):279–290 [2000]).

Inventive compositions can include negatively charged ternary complexes of cationic liposomes, transferrin or fusigenic peptide(s)or poly(ethylenimine). (E.g., Simoes, S. et al., *Gene delivery by negatively charged ternary complexes of DNA, cationic liposomes and transferrin or fusigenic peptides*, Gene Ther. 5(7):955–64 [1998]). Liposomal uptake-enhancing agents complexed with inventive polynucleotide(s) can also be encapsulated in polyethylene glycol (PEG), FuGENE6, or the like. (E.g., Saravolac, E. G., et al., *Encapsulation of plasmid DNA in stabilized plasmid-lipid particles composed of different cationic lipid concentration for optimal transfection activity*, J. Drug Target 7(6):423–37 [2000]; Yu, R. Z. et al., *Pharmacokinetics and tissue disposition in monkeys of an antisense oligonucleotide inhibitor of Ha-ras encapsulated in stealth liposomes*, Pharm Res. 16(8):1309–15 [1999]; Tao, M. et al., *Specific inhibition of human telomerase activity by transfection reagent, FuGENE6-antisense phophorothioate oligonucleotide complex in HeLa cells*, FEBS Lett 454(3):312–6 [1999]).

In some embodiments, the uptake of antisense oligonucleotides is also enhanced by complexation with biocompatible polymeric or co-polymeric nanoparticles, for example, comprising alginate, aminoalkylmethacrylate, methylmethacrylate, polymethylmethacrylate, methylaminoethyl-methacrylate, polyalkylcyanoacrylate (e.g., polyhexylcyanoacrylate), or the like. (E.g., Aynie, I. et al., *Spongelike alginate nanoparticles as a new potential system for the delivery of antisense oligonucleotides*, Antisense Nucleic Acid Drug Dev. 9(3):301–12 [1999]; Zimmer, A., *Antisense oligonucleotide delivery with polyhexylcyanoacrylate nanoparticles as carriers*, Methods 18(3): 286–95, 322 [1999]; Berton, M. et al., *Highly loaded nanoparticulate carrier using an hydrophobic antisense oligonucleotide complex*, Eur. J. Pharm. Sci. 9(2):163–70 [1999]; Zobel, H. P. et al., *Evaluation of aminoalkylmethacrylate nanoparticles as colloidal drug carrier systems. Part II: characterization of antisense oligonucleotides loaded copolymer nanoparticles*, Eur. J. Pharm. Biopharm. 48(1): 1–12 [1999]; Fattal, E. et al., *Biodegradable polyalkylcyanoacrylate nanoparticles for the delivery of oligonucleotides*, J. Controlled Release 53(1–3):137–43 [1998]).

Other useful uptake-enhancing agents for complexing with polynucleotides include starburst polyamidoamine (PAMAM) dendrimers. (E.g., Yoo, H. et al., *PAMAM dendrimers as delivery agents for antisense oligonucleotides*, Pharm. Res. 16(12):1799–804 [1999]; Bielinska, A. U. et al., *Application of membrane-based dendrimer/DNA complexes for solid phase transfection in vitro and in vivo*, Biomaterials 21(9):877–87 [2000]; Bielinska, A. U. et al., *DNA complexing with polyamidoamine dendrimers: implications for transfection*, Bioconjug. Chem. 10(5):843–50 [1999]; Bielinska, A. U et al., *Regulation of in vitro gene expression using antisense oligonucleotides or antisense expression plasmids transfected using starburst PAMAM dendrimers*, Nucleic Acid Res. 24(11):2176–82 [1996]; Kukowska-Latallo, J. F. et al., *Efficient transfer of genetic material into mammalian cells using Starburst polyamidoamine dendrimers*, Proc. Natl. Acad. Sci. USA 93(10):4897–902 [1996]; Delong, R. et al., *Characterization of complexes of oligonucleotides with polyamidoamine starburst dendrimers and effects on intracellular delivery*, J. Pharm. Sci. 86(6): 762–64 [1997]).

Other preferred uptake-enhancing agents include lipofectin, lipfectamine, DIMRIE C, Superfect, Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, or poly (ethylenimine) (PEI), and/or peptides, such as polylysine, protamine, pK17, peptide K8, and peptide p2 (E.g., Ferkol, Jr. et. al., U.S. Pat. Nos., 5,972,900 and 5,972,901; Vaysse, L. and Arveiler, B., *Transfection using synthetic peptides:* comparison of three DNA-compacting peptides and effect of centrifugation, Biochim Biophys Acta 1474(2):244–50 [2000]; Ni, Y. H. et al., *Protamine enhance the efficiency of liposome-mediated gene transfer in a cultured human hepatoma cell line*, J. Formos. Med. Assoc. 98(8):562–66 [1999]; Banerjee, R. et al., *Novel series of non-glycerol-based cationic transfection lipids for use in liposomal gene delivery*, J. Med. Chem. 42(21):4292–99 [1999]; Godbey, W. T. et al., *Improved packing of poly(ethylenimine/DNA complexes increases transfection efficiency*, Gene Ther. 6(8): 1380–88 [1999]; Kichler, A et al., *Influence of the DNA complexation medium on the transfection efficiency of lipospermine/DNA particles*, Gene Ther. 5(6):855–60 [1998];Birchaa, J. C. et al., *Physico-chemical characterisation and transfection efficiency of lipid-based gene delivery complexes*, Int. J. Pharm. 183(2):195–207 [1999]). These non-viral cellular uptake-enhancing agents have the advantage that they facilitate stable integration of xenogeneic DNA sequences into the vertebrate genome, without size restrictions commonly associated with virus-derived transfecting or transducing agents.

Another example, a viral cellular uptake-enhancing agent, is the adenovirus enhanced transferrin-polylysine-mediated gene delivery system has been described and patented by Curiel et al. (Curiel D. T., et al., *Adenovirus enhancement of transferrin-polylysine-mediated gene delivery*, PNAS USA 88: 8850–8854 (1991). The delivery of DNA depends upon endocytosis mediated by the transferrin receptor (Wagner et al., *Transferrin-polyvcation conjugates as carriers for DNA uptake into cells*, PNAS (USA) 87: 3410–3414 (1990). In addition this method relies on the capacity of adenoviruses to disrupt cell vesicles, such as endosomes and release the contents entrapped therein. This system can enhance the gene delivery to mammalian cells by as much as 2,000 fold over other methods.

The amount of each component of the composition is chosen so that the gene modification, e.g., by transfection or transduction, of a mammalian cell is optimized. Such optimization requires no more than routine experimentation. The ratio of polynucleotide to lipid is broad, preferably about 1:1, although other effective proportions can also be utilized depending on the type of lipid uptake-enhancing agent and polynucleotide utilized. (E.g., Banerjee, R. et al. [1999]; Jaaskelainen, I. et al., *A lipid carrier with a membrane active component and a small complex size are required for efficient cellular delivery of anti-sense phosphorothioate oligonucleotides*, Eur. J. Pharm. Sci. 10(3): 187–193 [2000]; Sakurai, F. et al., *Effect of DNA/liposome mixing ratio on the physicochemical characteristics, cellular uptake and intracellular trafficking of plasmid DNA/ cationic liposome complexes and subsequent gene expression*, J. Controlled Release 66(2–3):255–69 [2000]).

A suitable amount of the inventive polynucleotide to be delivered to the cells, in accordance with the method, preferably ranges from about 0.1 nanograms to about 1 milligram per gram of tumor tissue, in vivo, or about 0.1 nanograms to about 1 microgram per 5000 cells, in vitro. Suitable amounts for particular varieties of PTTG-C-related polynucleotides and/or cell types and/or for various mammalian subjects undergoing treatment, can be determined by routine experimentation. For example, malignant cell lines, such as MCF-7 or HeLa, typically are more efficiently transfected by the inventive PTTG-C-related polynucleotides than non-malignant cell lines. Also, those skilled in the art are aware that there is typically considerable variability among individual cancer patients to any single treatment regimen, therefore, the practitioner will tailor any embodiment of the inventive method to each individual patient as appropriate.

In some preferred embodiments, the polynucleotide can be delivered into the mammalian cell, either in vivo or in vitro using suitable expression vectors well-known in the art (e.g., retroviral vectors, adenovirus vectors, and the like). In addition, to inhibit the in vivo expression of PTTG, the introduction by expression vector of the antisense strand of a DNA encoding a PTTG-C peptide is contemplated.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA Appropriate expression vectors are well known to those of skill in the art and include those that are replicable in eukaryotic cells and/or prokaryotic cells and those that remain episomal or those which integrate into the host cell genome.

Exemplary, eukaryotic expression vectors, include the cloned bovine papilloma virus genome, the cloned genomes of the murine retroviruses, and eukaryotic cassettes, such as the pSV-2 gpt system (described by Mulligan and Berg, 1979, Nature Vol. 277:108–114) the Okayama-Berg cloning system (Mol. Cell Biol. Vol. 2:161–170, 1982), pGAL4, pCI (e.g., pCI-neo), and the expression cloning vector described by Genetics Institute (Science Vol. 228:810–815, 1985), are available which provide substantial assurance of at least some expression of the protein of interest in the transformed mammalian cell.

Particularly preferred are vectors which contain regulatory elements that can be linked to the inventive PTTG-encoding DNAs, such as a PTTG-C-encoding DNA segment, for transfection of mammalian cells. Examples are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In one embodiment of the present invention, adenovirus-transferrin/polylysine-DNA (TfAdpl-DNA) vector complexes (Wagner et al., 1992, PNAS, USA, 89:6099–6103; Curiel et al., 1992, Hum. Gene Therapy, 3:147–154; Gao et al., 1993, Hum. Gene Ther., 4:14–24) are employed to transduce mammalian cells with heterologous PTTG-specific nucleic acid. Any of the plasmid expression vectors described herein may be employed in a TfAdpl-DNA complex.

In addition, vectors may contain appropriate packaging signals that enable the vector to be packaged by a number of viral virions, e.g., retroviruses, herpes viruses, adenoviruses, resulting in the formation of a "viral vector."

"Virus", as used herein, means any virus, or transfecting fragment thereof, which can facilitate the delivery of the polynucleotide into mammalian cells. Examples of viruses which are suitable for use herein are adenoviruses, adeno-associated viruses, retroviruses such as human immune-deficiency virus, lentiviruses, mumps virus, and transfecting fragments of any of these viruses, and other viral DNA segments that facilitate the uptake of the desired DNA segment by, and release into, the cytoplasm of germ cells and mixtures thereof. A preferred viral vector is Moloney murine leukemia virus and the retrovirus vector derived from Moloney virus called vesicular-stomatitis-virus-glycoprotein (VSV-G)-Moloney murine leukemia virus. A most preferred viral vector is a pseudotyped (VSV-G) lentiviral vector derived from the HIV virus. (Naldini et al. [1996]). Also, the mumps virus is particularly suited because of its affinity for immature sperm cells including spermatogonia. All of the above viruses may require modification to render them non-pathogenic or less antigenic. Other known viral vector systems, however, are also useful within the confines of the invention.

Viral based systems provide the advantage of being able to introduce relatively high levels of the heterologous nucleic acid into a variety of cells. Suitable viral vectors for introducing inventive PTTG-specific polynucleotides into mammalian cells (e.g., vascular tissue segments) are well known in the art. These viral vectors include, for example, Herpes simplex virus vectors (e.g., Geller et al., 1988, Science, 241:1667–1669), Vaccinia virus vectors (e.g., Piccini et al., 1987, Meth. in Enzymology, 153:545–563, Cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78–84), Moloney murine leukemia virus vectors (Danos et al., 1980, PNAS, USA, 85:6469), adenovirus vectors (e.g., Logan et al., 1984, PNAS, USA, 81:3655–3659; Jones et al., 1979, Cell, 17:683–689; Berkner, 1988, Biotechniques, 6:616–626; Cotten et al., 1992, PNAS, USA, 89:6094–6098; Graham et al., 1991, Meth. Mol. Biol., 7:109–127), adeno-associated virus vectors, retrovirus vectors (see, e.g., U.S. Pat. Nos. 4,405,712 and 4,650,764), and the like. Especially preferred viral vectors are the adenovirus and retroviral vectors.

As used herein, "retroviral vector" refers to the well-known gene transfer plasmids that have an expression cassette encoding an heterologous gene residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764). Retroviral vectors include lentiviral vectors, such as HIV-derived vectors.

Suitable retroviral vectors for use herein are described, for example, in U.S. Pat. No. 5,252,479, and in WIPO publications WO 92/07573, WO 90/06997, WO 89/05345, WO 92/05266 and WO 92/14829, incorporated herein by reference, which provide a description of methods for efficiently introducing nucleic acids into human cells using such retroviral vectors. Other retroviral vectors include, for example, the mouse mammary tumor virus vectors (e.g., Shackleford et al., 1988, PNAS, USA, 85:9655–9659), and the like.

A most preferred embodiment employs a pseudotyped retroviral vector system, which was developed for gene therapy. (Naldini, L., et al., *In vivo gene delivery and stable transduction of nondividing cells by a lentiviral vector*, Science 272: 263–267 [1996]), and which is used to transduce mammalian cells. This gene delivery system employs retroviral particles generated by a three-plasmid expression system. In this system a packaging construct contains the human cytomegalovirus (hCMV) immediate early promoter, driving the expression of all viral proteins. The construct's design eliminates the cis-acting sequences crucial for viral packaging, reverse transcription and integration of these transcripts The second plasmid encodes a heterologous envelope protein (env), namely the G glycoprotein of the vesicular stomatitis virus (VSV-G). The third plasmid, the transducing vector (pHR'), contains cis-acting sequences of human immunodeficiency virus (HIV) required for packaging, reverse transcription and integration, as well as unique restriction sites for cloning heterologous complementary DNAs (cDNAs). For example, a genetic selection marker, such as green fluorescent protein (GFP), enhanced green fluorescent protein (EGFP), blue fluorescent protein, yellow fluorescent protein, β-galactosidase, and/or a gene encoding another preselected product is cloned downstream of the hCMV promoter in the HR' vector, and is operatively linked so as to form a transcriptional unit. A VSV-G pseudotyped retroviral vector system is capable of infecting a wide variety of cells including cells from different species and of integrating into the genome. Some retroviruses, i.e., lentiviruses, such as HIV, have the ability to infect non-dividing cells. Lentiviruses have a limited capacity for heterologous DNA sequences, the size limit for this vector being 7–7.5 kilobases (Verma, I. M. and Somia, N., *Gene Therapy—promises, problems and prospects*, Nature 389:239–242 [1997]). In vivo experiments with lentiviruses show that expression does not shut off like other retroviral vectors and that in vivo expression in brain, muscle, liver or pancreatic-islet cells, is sustained at least for over six months—the longest time tested so far (Verma and Somia [1997]; Anderson, W F., *Human Gene Therapy*, Nature (Suppl). 392:25–30 [1998]).

"Gene delivery (or transfection) mixture", in the context of this patent, means a selected PTTG carboxy-terminal-related polynucleotide, whether in sense or anti-sense orientation, together with an appropriate vector mixed, for example, with an effective amount of uptake-enhancing agent as described above. (E.g., Clark et al., *Polycations and cationic lipids enhance adenovirus transduction and transgene expression in tumor cells*, Cancer Gene Ther. 6(5): 437–46 [1999]). For example, the efficiency of adenoviral-, retroviral-, or lentiviral-mediated transduction is enhanced significantly by including a cationic lipid, such as polybrene during the infection.

In peptide-based embodiments of the inventive method of inhibiting neoplastic cellular proliferation and/or transformation, involves delivering an inventive composition comprising a PTTG carboxy-terminal peptide, which is interchangeably designated herein "PTTG-C" or "PTTG C-terminal peptide".

The terms "protein", "peptide", and "polypeptide" are used interchangeably herein. As used herein, the phrase "PTTG" refers to protein member of a mammalian family of PTTG proteins, formerly also known as "pituitary-tumor-specific-gene" (PTSG) proteins, that are able to transform mammalian cells in tissue culture (e.g., NIH 3T3 and the like).

In vivo, PTTG proteins are further characterized by having the ability to induce tumor formation, for example, in nude mice (e.g., when transfected into NIH 3T3 and the like). PTTG proteins include naturally occurring allelic variants thereof encoded by mRNA generated by alternative splicing of a primary transcript, and further include fragments thereof which retain at least one native biological activity.

The term "biologically active" or "functional", when used herein as a modifier of inventive PTTG protein(s), peptide (s), or fragments thereof, refers to a polypeptide that exhibits at least one of the functional characteristics attributed to PTTG. For example, one biological activity of PTTG is the ability to transform cells in vitro (e.g., NIH 3T3 and the like). Yet another biological activity of PTTG is the ability to induce neoplastic cellular proliferation (e.g., tumorigenesis) in nude mice (e.g., when transfected into NIH 3T3 cells and the like).

On the other hand, the inventive PTTG-C peptide, as distinct from the full length native PTTG protein, has the biological activity of inhibiting PTTG -mediated tumorigenesis in a dominant negative manner. "Dominant negative" is commonly used to describe a gene or protein which has a dominant effect similar to that described genetically, i.e. one copy of the gene gives a mutant phenotypic effect, and a negative effect in that it prevents or has a negative impact on a biological process such as a signal transduction pathway. Thus, PTTG carboxy-terminal peptides have the ability to downregulate intracellular PTTG expression and/or endogenous PTTG function. The inventive method is not limited to any particular biochemical, genetic, and/or physiological mechanism(s) by which a PTTG-C peptide exerts its biological activity on PTTG expression and/or PTTG function, and any or all such mechanism(s) can contribute to the biological activity of PTTG-C, in accordance with the invention.

any fragment of a larger PTTG-C molecule, which fragment retains PTTG-C biological activity with respect to down-regulating endogenous PTTG expression and/or endogenous PTTG function. Useful PTTG-C peptides are preferably, but not exclusively, about 15 to about 60 contiguous amino acid residues long and comprise one or more proline-rich regions, which are peptide segments having a PXXP motif, where the Xs between the proline (P) residues represent any amino acid residue, including proline. The proline-rich region(s) of the PTTG-C peptide is a potential SH3-binding site.

Most preferably, the PTTG-C peptide is derived from a human PTTG, also designated hPTTG or PTTG1 protein. The native human PTTG1 protein is 202 amino acids long, having the following amino acid sequence (Table 7 below; encoded by nucleotide positions 95 through 700 of human PTTG1 sequence SEQ. ID. NO.:3 and degenerate sequences).

TABLE 7

PTTG1 amino acid sequence.

| | | | | | | |
|---|---|---|---|---|---|---|
| 1 | MATLIYVDKE | NGEPGTRVVA | KDGLKLGSGP | SIKALDGRSQ | VSTPRFGKTF | (SEQ. ID. NO.:4) |
| 51 | DAPPALPKAT | RKALGTVNRA | TEKSVKTKGP | LKQKQPSFSA | KKMTEKTVKA | |
| 101 | KSSVPASDDA | YPEIEKFFPF | NPLDFESFDL | PEEHQIAHLP | LSGVPLMILD | |
| 151 | EERELEKLFQ | LGPPSPVKMP | SPPWESNLLQ | SPSSILSTLD | VELPPVCCDI | |
| 201 | DI | | | | | |

Another biological activity of PTTG or PTTG-C peptides is the ability to act as an immunogen for the production of polyclonal and monoclonal antibodies that bind specifically to PTTG and/or PTTG-C. Thus, an inventive nucleic acid encoding PTTG or PTTG-C will encode a polypeptide specifically recognized by an antibody that also specifically recognizes a PTTG protein as described herein. Such activity may be assayed by any method known to those of skill in the art. For example, a test-polypeptide encoded by a PTTG cDNA can be used to produce antibodies, which are then assayed for their ability to bind to the protein. If the antibody binds to the test-polypeptide and the protein with substantially the same affinity, then the polypeptide possesses the requisite biological activity with respect to immunogenicity.

In the method of inhibiting neoplastic cellular proliferation and/or transformation of a mammalian cell, whether in vitro or in vivo, useful PTTG-C peptides encompass also The human PTTG1 peptide is also encoded by any degenerate coding sequence encoding the amino acid sequence of SEQ. ID. NO.:4.

A preferred PTTG-C has the amino acid sequence corresponding to amino acid residues 147 through 202 of SEQ. ID. NO.:4 (Table 8 below; encoded by nucleotide positions 533 through 700 of SEQ. ID. NO.:3 or 1–168 of SEQ. ID. NO.:10 and degenerate sequences).

TABLE 8

Human PTTG-C amino acid sequence.

| | | | | | | |
|---|---|---|---|---|---|---|
| MILDEERELE | KLFQLGPPSP | VKMPSPPWES | NLLQSPSSIL | STLDVELPPV | CCDIDI | 56 | (SEQ. ID. NO.:9) |

There are at least two proline-rich regions between amino acid residues 163–173 of SEQ. ID. NO.:4, which correspond to amino acid residues 17 through 27 of SEQ. ID. NO.:9, encoded by nucleotides 49 through 81 of SEQ. ID. NO.:10 and degenerate sequences. Proline-rich regions are found at amino acid residues 163–167 and 170–173 of SEQ. ID. NO.:4, corresponding to amino acid residues 17–20 and 24–27 of SEQ. ID. NO.:9. Other useful smaller peptide fragments of SEQ. ID NO.:9 are tested by routine means for their effectiveness in inhibiting neoplastic cellular proliferation and/or transformation of a cell.

Another example of a PTTG protein is a rat PTTG having the following amino acid sequence (Table 9 below, encoded by nucleotide positions 293–889 of SEQ. ID. NO.:1 and degenerate sequences).

The amino acid sequence of SEQ. ID. NO.:16 includes proline-rich regions at amino acid residues 17–20, 24–27, and 34–37 (corresponding to amino acid residues 160–163, 167–170, and 177–180 of SEQ. ID. NO.:2).

TABLE 9

Rat PTTG amino acid sequence.

| | | | | | | | | | | | | | | | |
|---|---|---|---|---|---|---|---|---|---|---|---|---|---|---|---|
| Met | Ala | Thr | Leu | Ile | Phe | Val | Asp | Lys | Asp | Asn | Glu | Glu | Pro | Gly | Ser | 16 (SEQ. ID. NO.:2) |
| Arg | Leu | Ala | Ser | Lys | Asp | Gly | Leu | Lys | Leu | Gly | Ser | Gly | Val | Lys | Ala | 32 |
| Leu | Asp | Gly | Lys | Leu | Gln | Val | Ser | Thr | Pro | Arg | Val | Gly | Lys | Val | Phe | 48 |
| Gly | Ala | Pro | Gly | Leu | Pro | Lys | Ala | Ser | Arg | Lys | Ala | Leu | Gly | Thr | Val | 64 |
| Asn | Arg | Val | Thr | Glu | Lys | Pro | Val | Lys | Ser | Ser | Lys | Pro | Leu | Gln | Ser | 80 |
| Lys | Gln | Pro | Thr | Leu | Ser | Val | Lys | Lys | Ile | Thr | Glu | Lys | Ser | Thr | Lys | 96 |
| Thr | Gln | Gly | Ser | Ala | Pro | Ala | Pro | Asp | Asp | Ala | Tyr | Pro | Glu | Ile | Glu | 112 |
| Lys | Phe | Phe | Pro | Phe | Asp | Pro | Leu | Asp | Phe | Glu | Ser | Phe | Asp | Leu | Pro | 128 |
| Glu | Glu | His | Gln | Ile | Ser | Leu | Leu | Pro | Leu | Asn | Gly | Val | Pro | Leu | Met | 144 |
| Ile | Leu | Asn | Glu | Glu | Arg | Gly | Leu | Glu | Lys | Leu | Leu | His | Leu | Asp | Pro | 160 |
| Pro | Ser | Pro | Leu | Gln | Lys | Pro | Phe | Leu | Pro | Trp | Glu | Ser | Asp | Pro | Leu | 176 |
| Pro | Ser | Pro | Pro | Ser | Ala | Leu | Ser | Ala | Leu | Asp | Val | Glu | Leu | Pro | Pro | 192 |
| Val | Cys | Tyr | Asp | Ala | Asp | Ile. | | | | | | | | | | 199 |

A rat PTTG-C peptide includes amino acid residues 144 through 199 of SEQ. ID. NO.:2, i.e., SEQ. ID. NO.:16 (Table 10 below; encoded by nucleotide positions 722 through 889 of SEQ. ID. NO.:1 or 1–168 of SEQ. ID. NO.:18 and degenerate sequences).

Another example of a PTTG protein is a murine PTTG having the following amino acid sequence (Table 11 below; encoded by nucleotide positions 304 through 891 of SEQ. ID. NO.:15 and degenerate sequences).

TABLE 10

Rat PTTG-C amino sequence.

| | | | | | | | | | | | | | | | |
|---|---|---|---|---|---|---|---|---|---|---|---|---|---|---|---|
| Met | Ile | Leu | Asn | Glu | Glu | Arg | Gly | Leu | Glu | Lys | Leu | Leu | His | Leu | Asp | 16 SEQ. ID. NO.:16 |
| Pro | Pro | Ser | Pro | Leu | Gln | Lys | Pro | Phe | Leu | Pro | Trp | Glu | Ser | Asp | Pro | 32 |
| Leu | Pro | Ser | Pro | Pro | Ser | Ala | Leu | Ser | Ala | Leu | Asp | Val | Glu | Leu | Pro | 48 |
| Pro | Val | Cys | Tyr | Asp | Ala | Asp | Ile | | | | | | | | | 56 |

TABLE 11

Murine PTTG amino acid sequence.

| | |
|---|---|
| 1 MATLIFVDKD NEEPGRRLAS KDGLKLGTGV KALDGKLQVS TPRVGKVFNA | SEQ. ID. NO.: 14 |
| 51 PAVPKASRKA LGTVNRVAEK PMKTGKPLQP KQPTLTGKKI TEKSTKTQSS | |
| 101 VPAPDDAYPE IEKFFPFNPL DFDLPEEHQI SLLPLNGVPL ITLNEERGLE | |
| 151 KLLHLGPPSP LKTPFLSWES DPLYSPPSAL STLDVELPPV CYDADI | |

A murine PTTG-C peptide includes amino acid residues 141 through 196 of SEQ. ID. NO.:14, i.e., SEQ. ID. NO.:17 (Table 12 below; encoded by nucleotide positions 724 through 891 of SEQ. ID. NO.:15 or 1–168 of SEQ. ID. NO.:19 and degenerate sequences).

TABLE 12

Murine PTTG-C amino acid sequence.

ITLNEERGLE KLLHLGPPSP LKTPFLSWES DPLYSPPSAL STLDVELPPV CYDADI. 56 (SEQ. ID. NO.:17)

The amino acid sequence of SEQ. ID. NO.:17 includes a proline-rich region at amino acid residues 17–20 (corresponding to amino acid residues 157–160 of SEQ. ID. NO.:14).

Preferred PTTG-C peptides include:

(A) peptides having an amino acid sequence of (SEQ. ID. NO.:9), (SEQ. ID. NO.:16), or (SEQ. ID. NO.:17); or (B) mammalian PTTG-C peptides having at least about 60% sequence homology with any of the sequences in (A); or (C) peptide fragments of any of the sequences in (A) or (B) that comprise at least 15 contiguous amino acid residues and that function to downregulate endogenous PTTG expression and/or PTTG function. Most preferably, the fragment of (C) includes one or more proline-rich regions.

Those of skill in the art will recognize that in other useful PTTG-C peptides numerous residues of any of the above-described PTTG or PTTG-C amino acid sequences can be substituted with other, chemically, sterically and/or electronically similar residues without substantially altering PTTG or PTTG-C biological activity. In addition, larger polypeptide sequences containing substantially the same coding sequences as in SEQ ID NO:2, SEQ. ID. NO.:4, SEQ. ID. NO.:9, SEQ. ID. NO.:14, SEQ. ID. NO.:16, or SEQ. ID. NO.:17 (e g., splice variants) are contemplated.

As employed herein, the term "substantially the same amino acid sequence" refers to amino acid sequences having at least about 60% sequence homology or identity with respect to any of the amino acid sequences described herein ("reference sequences"), and retaining comparable functional and biological activity characteristic of the protein defined by the reference sequences described, particularly with respect to neoplastic cellular proliferation and/or transformation or its inhibition. More preferably, proteins having "substantially the same amino acid sequence" will have at least about 80%, still more preferably about 90% amino acid identity with respect to a reference amino acid sequence; with greater than about 95% amino acid sequence identity being especially preferred. It is recognized, however, that polypeptide containing less than the described levels of sequence identity arising as splice variants or that are modified by conservative amino acid substitutions are also encompassed within the scope of the present invention. The degree of sequence homology is determined by conducting an amino acid sequence similarity search of a protein data base, such as the database of the National Center for Biotechnology Information (NCBI; www.ncbi.nlm.nih gov/ BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data). (E.g., Altchul, S. F., et al., Gapped BLAST and PSI-BLAST: a new generation of protein database search programs, Nucleic Acids Res. 25(17):3389–402 [1997]; Zhang, J., & Madden, T. L., PowerBLAST: a new network BLAST application for interactive or automated sequence analysis and annotation, Genome Res 7(6):649–56 [1997]; Madden, T. L., et al., Applications of network BLAST server, Methods Enzymol. 266:131–41 [1996]; Altschul, S. F., et al., Basic local alignment search tool, J. Mol. Biol. 215(3):403–10 [1990]).

Also encompassed by the terms PTTG protein or PTTG-C peptide, respectively, are biologically functional or active peptide analogs thereof The term peptide "analog" includes any polypeptide having an amino acid residue sequence substantially identical to a sequence specifically shown herein in which one or more residues have been conservatively substituted with a functionally similar residue and which displays the ability to mimic the biological activity of PTTG or PTTG-C, respectively, particularly with respect to neoplastic cellular proliferation and/or transformation or its inhibition as described herein above Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue, provided that such polypeptide displays the requisite biological activity.

"Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The inventive polypeptide of the present invention also include any polypeptide having one or more additions and/or deletions of residues, relative to the sequence of a polypeptide whose sequence is shown herein, so long as the requisite PTTG or PTTG-C biological activity is maintained.

In accordance with peptide-based embodiments of the inventive method of inhibiting neoplastic cellular proliferation and/or transformation, the composition comprising the PTTG-C peptide is delivered to the cell. A suitable amount of the inventive PTTG-C peptide to be delivered to the cells, in accordance with the method, preferably ranges from about 0.1 nanograms to about 1 milligram per gram of tumor tissue, in vivo, or about 0.1 nanograms to about 1 microgram per 5000 cells, in vitro. Suitable amounts for particular varieties of PTTG-C peptide and/or cell types and/or for various individual mammalian subjects undergoing treatment, can be determined by routine experimentation.

Methods of delivering and importing peptides into target cells are known. For example, the composition preferably, but not necessarily, comprises in addition to the PTTG-C peptide, a complex in which the PTTG-C peptide is complexed with a cellular uptake-enhancing agent. For example, the PTTG-C peptide can be covalently linked in a complex to a cellular uptake-enhancing and/or importation-competent peptide segment for delivery of PTTG-C into the mammalian cell; in addition, a nuclear localization peptide can be included in the complex to direct the PTTG-C to the nucleus. (E.g., Lin et al., *Method for importing biologically active molecules into cells*, U.S. Pat. No. 6,043,339). An "importation-competent peptide," as used herein, is a sequence of amino acids generally of a length of about 10 to about 50 or more amino acid residues, many (typically about 55–60%) residues of which are hydrophobic such that they have a hydrophobic, lipid-soluble portion. The hydrophobic portion is a common, major motif of a signal peptide, and it is often recognizable as a central part of the signal peptide of a protein secreted from cells. A signal peptide is a peptide capable of penetrating through the cell membrane to allow the export of cellular proteins. Signal peptides useful in the present method are also "importation-competent," i.e., capable of penetrating through the cell membrane from outside the cell to the interior of the cell.

In a preferred embodiment, a PTTG-C peptide forms first PTTG-C peptide segment of a chimeric or fusion protein. The chimeric or fusion protein comprises at least the first PTTG-C peptide segment and a second cellular uptake-enhancing and/or importation-competent peptide segment. The second segment of the chimeric or fusion protein is a cellular uptake-enhancing and/or importation-competent peptide segment, such as a signal peptide, that allows the hybrid molecule to enter neoplastic cells that overexpress PTTG, whether in vitro or in vivo. The second peptide segment, such as the human immunodeficiency virus (HIV) TAT protein (Schwarze, S. R., et al., *In vivo protein transduction: delivery of a biologically active protein into the mouse*, Science 285: 1569–72 [1999]), infiltrates the cells, and once within the cells, the PTTG-C peptide segment of the fusion protein becomes active within the cells to inhibit endogenous PTTG expression and/or PTTG function. Another example of a useful uptake-enhancing peptide segment is the signal peptide from Kaposi fibroblast growth factor (K-FGF). But any cellular uptake-enhancing and/or importation-competent peptide segment, capable of translocating across the cell membrane into the interior of the selected target mammalian cell, can be used according to this invention. The chimeric or fusion protein can also include additional segments, such as a linker segment, that can be an intervening segment between the first and second segments. The additional segment can alternatively be a terminal segment, as appropriate.

In embodiments of the method involving the use of PTTG-C chimeric or fusion proteins, the cellular uptake-enhancing and/or importation-competent peptide segment can be the uptake-enhancing agent. Alternatively, or in addition, the cellular uptake-enhancing agent can be a lipid or liposome uptake-enhancing agent as described herein above, such as lipofectin, lipofectamine, DOTAP, and others. Cationic (or polycationic) lipids or liposomes can also be complexed with a signal peptide and a negatively-charged biologically active molecule by mixing these components and allowing them to charge-associate. Anionic liposomes generally are utilized to encapsulate within the liposome the substances to be delivered to the cell. Procedures for forming cationic liposome- encapsulating substances are standard in the art and can readily be utilized herein by one of ordinary skill in the art to encapsulate the complex of this invention. For example, liposome uptake-enhancing agents complexed with inventive PTTG-C peptide fragments can be encapsulated in polyethylene glycol (PEG), FuGENE6, or the like.

With respect to delivery of the composition to mammalian cells in vivo, the composition is administered to a mammalian subject in need of treatment, including a human subject, by any conventional delivery route. Preferably, the PTTG-C peptide, whether or not complexed with cellular uptake-enhancing and/or importation-competent peptides (e.g., signal or localization peptides), is injected intravenously, intra-arterially, intraperitoneally, or by means of injection directly into a tumor or into a cell by microinjection. Conventional stereotactic methods can be useful for direct injection into tumors or cells. In other preferred embodiments, controlled release formulations of biodegradable polymeric microspheres or nanospheres (e.g., polylactide-co-glycolide; PLGA) encapsulating the PTTG-C peptide, or PTTG-C chimeric or fusion protein are administered to the mammalian subject orally. (E.g., Zhu, G. et al., *Stabilization of proteins encapsulated in injectable poly(lactide-co-glycolide)*, Nature Biotechnology 18:52–57 [2000]). Administration by nasal, rectal, or vaginal delivery routes can also be useful. Administration by catheter or stent can also be useful for delivering the PTTG-C peptide.

In some embodiments, isolated and crystallized PTTG-C peptide can be cross-linked with a multifunctional crosslinking agent that inhibits proteolysis of the PTTG-C peptide in vivo. (Navia, M. A., *Method of protein therapy by orally administering crosslinked protein crystals*, U.S. Pat. No. 6,011,001).

In accordance with the inventive method of inhibiting neoplastic cellular proliferation and/or transformation that is mediated by PTTG, the mammalian cell is a cell that overexpresses PTTG, the gene that encodes a PTTG protein Although detecting PTTG overexpression by the cell is not essential or necessary to the practice of the inventive method, the level of PTTG expression, including overexpression, is detectable by one skilled in the art. Detection of PTTG expression is accomplished by immunochemical assay for PTTG protein, for example, using the inventive anti-PTTG-C antibodies, described herein, or other anti-PTTG-specific antibodies. Alternatively, amplification of PTTG-specific mRNAs present in biological samples (e.g., tissue biopsy) can be used to detect PTTG expression. This is done by known molecular biological techniques of amplification and analysis of the amplification products for the presence or absence of PTTG-specific amplification products. If PTTG gene-specific amplification products are present, the findings are indicative of expression of the PTTG gene and diagnostic of the presence of neoplastic cellular proliferation in the subject as defined herein.

However, for interpretation of negatives (no PTTG-specific amplification products) analysis is preferably carried out following a control amplification of nucleic acids specific for a housekeeping gene, for example, a gene encoding β-actin, phosphofructokinase (PFK), glyceraldehyde 3-phosphate dehydrogenase, or phosphoglycerate kinase. Only if expression of the housekeeping gene is detected in the sample, is the absence of PTTG gene expression reliably accepted. With increasing sensitivity of amplification and analysis methods employed, it becomes increasingly preferable to determine the level of PTTG gene expression relative to expression of a housekeeping gene, in order to better distinguish neoplastic, hyperplastic, cytologically dysplastic and/or premalignant cellular growth or proliferation from the detectable background of normal cellular division. The ratio of PTTG expression to housekeeping gene expression is determined, for example, by real-time PCR methods or densitometric measurement and analysis of electrophoretic bands after amplification. When the ratio of PTTG expression to housekeeping gene expression exceeds a normal cell standard range and/or approximates an abnormal (e.g., neoplastic) cell standard range, this indicates overexpression of PTTG gene product, characteristic of neoplastic, hyperplastic, cytologically dysplastic and/or premalignant cellular growth or proliferation.

PTTG-specific mRNAs in a biological sample are amplified by a suitable amplification method. For example, a reverse transcriptase-mediated polymerase chain reaction (RT-PCR) is employed to amplify PTTG-specific nucleic acids. Briefly, two enzymes are used in the amplification process, a reverse transcriptase to transcribe PTTG-specific cDNA from a PTTG-specific mRNA template in the sample, a thermal resistant DNA polymerase (e.g., Taq polymerase), and PTTG-specific primers to amplify the cDNA to produce PTTG gene-specific amplification products. The use of limited cycle PCR yields semi-quantitative results. (E.g., Gelfand et al., *Reverse transcription with thermostable DNA polymerase-high tempreature reverse transcription*, U.S. Pat. Nos. 5,310,652; 5,322,770; Gelfand et al., *Unconventional nucleotide substitution in temperature selective RT-PCR*, U.S. Pat. No. 5,618,703).

Alternatively, single enzyme RT-PCR is employed to amplify PTTG gene-specific nucleic acids. Single enzymes now exist to perform both reverse transcription and polymerase functions, in a single reaction. For example, the Perkin Elmer recombinant *Thermus thermophilus* (rTth) enzyme(Roche Molecular), or other similar enzymes, are commercially available.

Real-time RT-PCR can be employed to amplify PTTG-specific nucleic acids. Briefly, this is a quantitative gene analysis based on the ratio of PTTG gene expression and the expression of a housekeeping gene, i.e., a gene that is expressed at about the same level in normal and abnormal (e.g., malignant) cells, for example, a gene encoding β-actin, phosphofructokinase, glyceraldehyde 3-phosphate dehydrogenase, or phosphoglyceratekinase. The the ratio of the PTTG and housekeeping genes' expressions is routinely established as a standard for normal and abnormal cells, which standard expression ratio(s) is (are) used for comparison in determining that expression of the PTTG gene relative to expression of the "housekeeping" gene in a given sample is either "normal" or "increased", the latter indicative of"overexpression" and diagnostic for the presence of neoplastic, hyperplastic, cytologically dysplastic and/or premalignant cellular growth or proliferation. In this embodiment, the ratio is the key to diagnosis and constitutes quantitative gene expression analysis. This embodiment utilizes so-called real-time quantitative PCR, carried out with commercially available instruments, such as the Perkin Elmer ABI Prism 7700, the so-called Light Cycler (Roche Molecular), and/or other similar instruments. Optionally, single enzyme RT-PCR technology, for example, employing rTth enzyme, can be used in a real-time PCR system. Preferably, amplification and analysis are carried out in an automated fashion, with automated extraction of mRNA from a urine sediment sample, followed by real-time PCR, and fluorescence detection of amplification products using probes, such as TaqMan or Molecular Beacon probes. Typically, the instrumentation includes software that provides quantitative analytical results during or directly following PCR without further amplification or analytical steps.

Alternatively, transcription-mediated amplification (TMA) is employed to amplif PTTG gene-specific nucleic acids. (E.g., K. Kamisango et al., *Quantitative detection of hepatitis B virus by transcription-mediated amplification and hybridization protection assay*, J. Clin. Microbiol. 37(2):310–14 [1999]; M. Hirose et al., *New method to measure telomerase activity by transcription-mediated amplification and hybridization protection assay*, Clin. Chem. 44(12) 2446–52 [1998]). Rather than employing RT-PCR for the amplification of a cDNA, TMA uses a probe that recognizes a PTTG-specific (target sequence) RNA; in subsequent steps, from a promoter sequence built into the probe, an RNA polymerase repetitively transcribes a cDNA intermediate, in effect amplifying the original RNA transcripts and any new copies created, for a level of sensitivity approaching that of RT-PCR. The reaction takes place isothermally (one temperature), rather than cycling through different temperatures as in PCR.

Other useful amplification methods include a reverse transcriptase-mediated ligase chain reaction (RT-LCR), which has utility similar to RT-PCR. RT-LCR relies on reverse transcriptase to generate cDNA from mRNA, then DNA ligase to join adjacent synthetic oligonucleotides after they have bound the target cDNA.

Amplification of a PTTG gene-specific nucleic acid segment of the subject can be achieved using PTTG gene-specific oligonucleotide primers and primer sets as provided herein.

Optionally, high throughput analysis may be achieved by PCR multiplexing techniques well known in the art, employing multiple primer sets, for example primers directed not only to PTTG gene-specific nucleic acids, but to amplifying expression products of housekeeping genes (controls) or of other potential diagnostic markers (e.g., oncogenes), as well; such as MAG or telomerase, to yield additional diagnostic information. (E.g., Z. Lin et al., *Multiplex genotype determination at a large number of gene loci*, Proc. Natl. Acad. Sci. USA 93(6):2582–87 [1996]; Demetriou et al., *Method and probe for detection of gene associated with liver neoplastic disease*, U.S. Pat. No. 5,866,329).

Hybridization analysis is a preferred method of analyzing the amplification products, employing one or more PTTG-specific probe(s) that, under suitable conditions of stringency, hybridize(s) with single stranded PTTG-specific nucleic acid amplification products comprising complementary nucleotide sequences. Hybridization refers to the binding of complementary strands of nucleic acid (i.e., sense:antisense strands or probe:target-DNA) to each other through hydrogen bonds, similar to the bonds that naturally occur in chromosomal DNA. The amplification products are typically deposited on a substrate, such as a cellulose or nitrocellulose membrane, and then hybridized with labeled PTTG-specific probe(s), optionally after an electrophoresis. Conventional dot blot, Southern, Northern, or fluorescence in situ (FISH) hybridization protocols, in liquid hybridization, hybridization protection assays, or other semi-quantitative or quantitative hybridization analysis methods are usefully employed along with the PTTG gene-specific probes of the present invention. Preferred probe-based hybridization conditions comprise a temperature of about 37° C., a formamide concentration of about 20%, and a salt concentration of about 5×standard saline citrate (SSC; 20×SSC contains 3 M sodium chloride, 0.3 M sodium citrate, pH 7.0) Such conditions will allow the identification of sequences which have a substantial degree of similarity with the probe sequence, without requiring perfect homology. The phrase "substantial similarity" refers to sequences which share at least 50% homology. Stringency levels used to hybridize a given probe with target-DNA can be readily varied by those of skill in the art. Preferably, hybridization conditions will be selected which allow the identification of sequences having at least about 60% homology with the probe, while discriminating against sequences which have a lower degree of homology with the probe.

As used herein, a "probe" is single-stranded DNA or RNA, or a nucleic acid analog. The inventive probe is preferably 7 to 500 nucleotides long, more preferably 14 to 150 nucleotides long, and most preferably at least 50 nucleotides long. The probe comprises, for at least part of its length, a PTTG-specific nucleotide sequence at least 7 to 15 contiguous nucleotides long, such that the probe hybridizes to a PTTG-specific single stranded nucleic acid under suitably stringent hybridization conditions. Examples of PTTG-specific nucleotide sequences are set forth in any of SEQ. ID. NOS.:1, 3, 10, 15, 18, or 19, preferably, but not necessarily, including 5' and/or 3' coding regions thereof. In addition, the entire cDNA encoding region of an inventive PTTG-specific nucleotide sequence, or the entire sequence corresponding to SEQ. ID. NOS.:1, 3, 10, 15, 18, 19, or nucleotide sequences complementary to any of these, can be used as a probe. For example, probes comprising inventive oligonucleotide primer sequences, such as, but not limited to, SEQ. ID. NO.:8, can be labeled for use as probes for detecting or analyzing PTTG-specific nucleic acid amplification products. Any of the inventive isolated PTTG-C-related polynucleotides can be used as probes or primers.

Alternatively, electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence. (K. Keparnik et al., *Fast detection of a (CA) 18 microsatellite repeat in the IgE receptor gene by capillary electrophoresis with laser-induced fluorescence detection*, Electrophoresis 19(2);249–55 [1998]; H. Inoue et al., *Enhanced separation of DNA sequencing products by capillary electrophoresis using a stepwise gradient of electric field strength*, J. Chromatogr. A. 802(1):179–84 [1998]; N. J. Dovichi, *DNA sequencing by capillary electrophoresis*, Electrophoresis 18(12–13):2393–99 [1997]; H Arakawa et al., *Analysis of single-strand conformation polymorphisms by capillary electrophoresis with laser induced fluorescence detection*, J. Pharm. Biomed. Anal. 15(9–10):1537–44 [1997]; Y. Baba, *Analysis of disease-causing genes and DNA-based drugs by capillary electrophoresis. Towards DNA diagnosis and gene therapy for human diseases*, J. Chromatgr B. Biomed. Appl. 687(2):271–302 [1996]; K. C. Chan et al., *High-speed electrophoretic separation of DNA fragments using a short capillary*, J. Chromatogr B. Biomed. Sci. Appl. 695(1):13–15 [1997]). Probes can be labeled by methods well-known in the art.

As used herein, the terms "label", "tracer", and "indicating means" in their various grammatical forms refer to single atoms and molecules that are either directly or indirectly involved in the production of a detectable signal. Any label or indicating means can be linked to PTTG-specific probes, primers, or amplification products, or PTTG proteins, peptides, peptide fragments, or anti-PTTG antibody molecules. The label can be used alone or in conjunction with additional reagents. Such labels are themselves well-known in the art. The label can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in Antibody As a Tool, Marchalonis et al., eds., John Wiley & Sons, Ltd., pp. 189–231 (1982), which is incorporated herein by reference. Any of diverse fluorescent dyes can optionally be used as a label, including but not limited to, SYBR Green I, Y1O-PRO-1, thiazole orange, Hex (i.e., 6-carboxy-2',4',7',4,7-hexachlorofluoroscein), pico green, edans, fluorescein, FAM (i.e., 6-carboxyfluorescein), or TET (i.e., 4,7,2',7'-tetrachloro-6-carboxyfluoroscein). (E.g., J. Skeidsvoll and P. M. Ueland, *Analysis of double-stranded DNA by capillary electrophoresis with laser-induced fluorescence detection using the monomeric dye SYBR green I*, Anal. Biochem. 231(20):359–65 [1995]; H. Iwahana et al., *Multiple fluorescence-based PCR-SSCP analysis using internal fluorescent labeling of PCR products*, Biotechniques 21(30:510–14, 516–19 [1996]).

The label can also be an enzyme, such as horseradish peroxidase (HRP), glucose oxidase, β-galactosidase, and the like. Alternatively, radionuclides are employed as labels. The linking of a label to a substrate, i.e., labeling of nucleic acid probes, antibodies, polypeptide, and proteins, is well known in the art. For instance, an inventive antibody can be labeled by metabolic incorporation of radiolabeled amino acids provided in the culture medium. See, for example, Galfre et al., Meth. Enzymol., 73–3–46 (1981). Conventional means of protein conjugation or coupling by activated functional groups are particularly applicable. See, for example, Aurameas et al., Scand. J. Immunol., Vol. 8, Suppl. 7:7–23 (1978), Rodwell et al., Biotech., 3:889–894 (1984), and U.S. Pat. No. 4,493,795.

In accordance with yet another embodiment of the present invention, there are provided anti-PTTG antibodies having specific reactivity with PTTG polypeptides of the present invention. Antibody fragments, for example Fab, Fab', F(ab')$_2$, or F(v) fragments, that selectively or specifically bind a PTTG protein, PTTG-C peptide, or immunogenic fragment of PTTG-C, are also encompassed within the definition of "antibody".

Inventive antibodies can be produced by methods known in the art using PTTG polypeptide, proteins or portions thereof, such as PTTG-C peptide or immunogenic fragments of PTTG-C, as antigens. For example, polyclonal and monoclonal antibodies can be produced by methods well known in the art, as described, for example, in Harlow and Lane, *Antibodies: A Laboratory Manual* (Cold Spring Harbor Laboratory [1988]), which is incorporated herein by reference. Isolated or purified PTTG proteins, PTTG-C peptides, and immunogenic PTTG-C fragments can be used as immunogens in generating such specific antibodies.

PTTG proteins, PTTG-C peptides, or polypeptide analogs thereof, are purified or isolated by a variety of known biochemical means, including, for example, by the recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol.182, (Academic Press, [1990]), which is incorporated herein by reference. Isolated PTTG proteins or PTTG-C peptides are free of cellular components and/or contaminants normally associated with a native in vivo environment Isolated PTTG proteins or PTTG-C peptides can also be chemically synthesized For example, synthetic polypeptide can be produced using Applied Biosystems, Inc. Model 430A or 431A automatic peptide synthesizer (Foster City, Calif.) employing the chemistry provided by the manufacturer. Alternatively, PTTG can be isolated or purified from native sources, and PTTG-C peptides can be isolated from PTTG (or from chimeric proteins) by the use of suitable proteases.

Alternatively, PTTG or PTTG-C polypeptides can be recombinantly derived, for example, produced by mammalian cells genetically modified to express PTTG-C-encoding polynucleotides in accordance with the inventive technology as described herein. Recombinant methods are well known, as described, for example, in Sambrook et al., supra., 1989). An example of the means for preparing the inventive PTTG or PTTG-C polypeptide(s) is to express nucleic acids encoding the PTTG protein or PTTG-C peptide in a suitable host cell, such as a bacterial cell, a yeast cell, an amphibian cell (i.e., oocyte), or a mammalian cell, such as the inventive mammalian host cell described herein below, using methods well known in the art, and recovering the expressed polypeptide, again using well-known methods.

The immunogenicity of various PTTG-C fragments of interest is determined by routine screening. Alternatively, synthetic PTTG or PTTG-C polypeptides or fragments thereof can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 [1991]; Ausubel et al., *Current Protocols in Molecular Biology* (John Wiley and Sons, NY [1989] which are incorporated herein by reference).

Antibody so produced can be used, inter alia, in diagnostic or assay methods and systems to detect the level of PTTG protein, PTTG-C peptide, or immunogenic fragments thereof, present in a mammalian, preferably human, biological sample, such as tissue or vascular fluid.

This is useful, for example, in determining the level of PTTG expression. Such antibodies can also be used for the immunoaffinity or affinity chromatography purification of the inventive PTTG proteins or PTTG-C peptides. In addition, methods are contemplated herein for detecting the presence of PTTG protein or PTTG-C peptide, either on the surface of a cell or within a cell (such as within the nucleus), which methods comprise contacting the cell with an antibody that specifically binds to PTTG protein or PTTG-C peptide, under conditions permitting specific binding of the antibody to PTTG protein or PTTG-C peptide, detecting the presence of the antibody bound to PTTG or PTTG-C, and thereby detecting the presence of PTTG or PTTG-C polypeptide on the surface of, or within, the cell. With respect to the detection of such polypeptide, the antibodies can be used for in vitro diagnostic or assay methods, or in vivo imaging methods.

Immunological procedures useful for in vitro detection of target PTTG or PTTG-C polypeptides in a sample include immunoassays that employ a detectable antibody. Such immunoassays include, for example, ELISA, immunofluorescence assay (IFA), Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionuclides, enzymes, fluorogens, chromogens and chemiluminescent labels.

Inventive anti-PTTG or anti-PTTG-C antibodies are also contemplated for use herein to modulate activity of the PTTG polypeptide in living animals, in humans, or in biological tissues or fluids isolated therefrom. Accordingly, compositions comprising a carrier and an amount of an antibody having specificity for PTTG polypeptide effective to block naturally occurring ligands or other PTTG-binding proteins from binding to invention PTTG polypeptide are contemplated herein. For example, a monoclonal antibody directed to an epitope of PTTG polypeptide molecules present on the surface of a cell and having an amino acid sequence substantially the same as an amino acid sequence for a cell surface epitope of a PTTG polypeptide including the amino acid sequence shown in SEQ ID NOS:2, 4, 9, 14, 16, or 17 can be useful for this purpose.

The present invention also relates to transfected, transduced, or otherwise transformed mammalian host cells comprising any of the inventive PTTG-C-related polynucleotide-containing compositions as described herein above. The inventive cells are either contained in a mammalian subject or are cultured in vitro. Included among preferred embodiments are mammalian host cells containing an expression vector comprising the inventive PTTG-C-related polynucleotide in a transcriptional unit. Preferably, a product is expressed by the cell, which product, most preferably, but not necessarily, is a biologically active PTTG-C peptide that functions to downregulate PTTG-mediated neoplastic cellular proliferation and/or transformation. In vitro and in vivo methods of transfecting, transducing, or transforming suitable host cells are generally known in the art. Methods for culturing cells, in vitro, are also well known. Exemplary methods of transfection, transduction, or transformation include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394, 448 and 4,619,794), cytofection, microparticle bombardment, and the like. The heterologous nucleic acid can optionally include sequences which allow for its extrachromosomal (i.e., episomal) maintenance, or heterologous DNA can be caused to integrate into the genome of the host (as an alternative means to ensure stable maintenance in the host cell).

The present invention further provides transgenic non-human mammals containing the inventive mammalian cells that are capable of expressing exogenous nucleic acids encoding PTTG polypeptides, particularly the inventive PTTG-C peptides and functional fragments thereof as described hereinabove. As employed herein, the phrase "exogenous nucleic acid" refers to nucleic acid sequence which is not native to the host, or which is present in the host in other than its native environment (e.g., as part of a genetically engineered DNA construct). Methods of producing transgenic non-human mammals are known in the art. Typically, the pronuclei of fertilized eggs are microinjected in vitro with foreign, i.e., xenogeneic or allogeneic DNA or hybrid DNA molecules, and the microinjected fertilized eggs are then transferred to the genital tract of a pseudopregnant female to gestate to term. (E.g., P. J. A. Krimpenfort et al., *Transgenic mice depleted in mature T-cells and methods for making transgenic mice*, U.S. Pat. Nos. 5,175,384 and 5,434,340; P. J. A. Krimpenfort et al., *Transgenic mice depleted in mature lymphocytic cell-type*, U.S. Pat. No. 5,591,669). Alternatively, methods for producing transgenic non-human mammals can involve genetic modification of female or male germ cells using an expression vector, which germ cells are then used to produce zygotes, which are gestated to term. The resulting offspring are selected for the desired phenotype. These offspring can further be bred or cloned to produce additonal generations of transgenic animals with the desired phenotype. The inventive transgenic non-human mammals, preferably, but not necessarily, are large animals such as bovines, ovines, porcines, equines, and the like, that produce relatively large quantities of PTTG-C peptides that can be harvested for use in practicing the method of inhibiting neoplastic cellular proliferation and/or transformation.

Most preferably, the transgenic non-human mammal is a female that produces milk into which the inventive PTTG-C peptides have been secreted. The PTTG-C peptides are then purified from the milk. (E.g., Christa, L., et al., *High expression of the human hepatocarcinoma-intestine-pancreas/pancreatic-associated protein (HIPPAP) gene in the mammary gland of lactating transgenic mice secretion into the milk and purification of the HIP/PAP lectin*, Eur. J. Biochem. 267(6):1665–71 [2000]; Sobolev, A. S. et al., *Receptor-mediated transfection of murine and ovine mammary glands in vivo*, J. Biol. Chem. 273(14):7928–33 [1998]; Zhang, K. et al., *Construction of mammary gland-specific expression vectors for human clotting factor IX and its secretory expression in goat milk*, Chin. J. Biotechnol. 13(4):271–6 [1997]; Clark, A. J., *Gene expression in the mammary glands of transgenic animals*, Biochem. Soc. Symp. 63:133–40 [1998]; Niemann, H. et al., *Expression of human blood clotting factor VIII in the mammary gland of transgenic sheep*, Transgenic Res. 8(3):237–47 [1999]).

Techniques for obtaining the preferred transgenic female mammals typically employ transfection with an expression vector in which, within a transcriptional unit regulated, for example, by a suitable β-lactoglobulin promoter, the PTTG-C peptide-encoding polynucleotide is chimerically linked with a polynucleotide encoding a mammary secretory signal peptide, such that mammary-specific expression yields a chimeric polypeptide from which the desired PTTG-C peptide segment is removed proteolytically and purified.

The present invention is also directed to a kit for the treatment of neoplastic cellular proliferation. The kit is useful for practicing the inventive method of inhibiting neoplastic cellular proliferation and/or transformation. The kit is an assemblage of materials or components, including at least one of the inventive compositions containing a PTTG-C-related polynucleotide and/or PTTG-C peptides, as described above. The exact nature of the components configured in the inventive kit depends on its intended purpose. For example, some embodiments of the kit are configured for the purpose of treating cultured mammalian cells. Other embodiments are configured for the purpose of treating mammalian cells in vivo, i.e., for treating mammalian subjects in need of treatment, for example, subjects with malignant tumors. In a most preferred embodiment, the kit is configured particularly for the purpose of treating human subjects.

Instructions for use are also included in the kit. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like, typically for an intended purpose.

Optionally, the kit also contains other useful components, such as, diluents, buffers, pharmaceutically acceptable carriers, specimen containers, syringes, stents, catheters, pipetting or measuring tools, paraphernalia for concentrating, sedimenting, or fractionating samples, or the inventive antibodies, and/or primers and/or probes for controls.

The materials or components assembled in the kit can be provided to the practitioner stored in any convenient and suitable ways that preserve their operability and utility. For example the components can be in dissolved, dehydrated, or lyophilized form, they can be provided at room, refrigerated or frozen temperatures.

The components are typically contained in suitable packaging material(s). As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment.

The packaging materials employed in the kit are those customarily utilized in polynucleotide-based or peptide-based systems. As used herein, the term "package" refers to a suitable solid matrix or material such as glass, plastic, paper, foil, and the like, capable of holding the individual kit components. Thus, for example, a package can be a glass vial used to contain suitable quantities of an inventive composition containing nucleic acid or peptide components. The packaging material generally has an external label which indicates the contents and/or purpose of the kit and/or its components.

The invention will now be described in greater detail by reference to the following non-limiting examples, which unless otherwise stated were performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol.152, S. L. Berger and A. R. Kimmerl Eds., Academic Press Inc., San Diego, USA (1987).

EXAMPLES

Example 1

Isolation of PTTG cDNA

To clarify the molecular mechanisms involved in pituitary tumorigenesis, differential display PCR was used to identify mRNAs differentially expressed in pituitary tumor cells (see, e g., Risinger et al., 1994, Molec. Carcinogenesis, 11:13–18; and Qu et al., 1996, Nature, 380:243–247). GC and $GH_4$ pituitary tumor cell lines (ATCC #CCL-82 and #CCL-82.1, respectively) and an osteogenic sarcoma cell line UM108 (ATCC #CRL-1663) were grown in DMEM supplemented with 10% fetal bovine serum. Normal Sprague-Dawley rat pituitaries were freshly excised. Total RNA was extracted from tissue cultured cells and pituitary tissue using RNeaSy™ kit (Qiagen) according to manufacturer's instructions. Trace DNA contamination in RNA preparations was removed by DNaseI (GenHunter Corporation) digestion. cDNA was synthesized from 200 ng total RNA using MMLV reverse transcriptase (GenHunter Corporation), and one of the three anchored primers (GenHunter Corporation). The cDNA generated was used in the PCR display.

Three downstream anchored primers $AAGCT_{11}N$ (SEQ. ID. NO.:13; where N may be A, G, or C), were used in conjunction with 40 upstream arbitrary primers for PCR display. 120 primer pairs were used to screen mRNA expression in pituitary tumors versus normal pituitary. One tenth of the cDNA generated from the reverse transcriptase reaction was amplified using AmpliTaq DNA polymerase (Perkin Elmer) in a total volume of 20 $\mu$l containing 10 mM Tris, pH 8,4, 50 mM KCl, 1.5 mM $MgCl_2$, 0.001% gelatin, 2 $\mu$M dNTPs, 0.2 $\mu$M each primer and 1 $\mu$l [$^{35}$S]dATP. PCR cycles consisted of 30 seconds at 94° C., 2 minutes at 40° C., and 30 seconds at 72° C. for 40 cycles. The products were separated on 6% sequencing gels, and dried gels were exposed to Kodak film for 24 to 48 hours.

After development, DNA fragments amplified from pituitary tumor and normal pituitary were compared. Bands unique to pituitary tumor were excised from the gel, and DNA extracted by boiling in 100 $\mu$l water and precipitated with ethanol in the presence of glycogen (GenHunter Corporation). DNA was reamplified using the original set of primers and the same thermal cycling conditions except that the dNTP concentration was increased to 20 $\mu$M. Reaction products were run on 1% agarose gel and stained with ethidium bromide. Bands were excised from the gel, eluted (Qiagen), cloned in to TA vectors (Invitrogen) and sequenced using sequenase (USB). Using 120 primer pairs in the above-described PCR assay, 11 DNA bands that appeared to be differentially expressed in pituitary tumor cells were identified. These bands were evaluated further by Northern blot analysis, using the PCR products as probes.

For Northern blot analysis, 20 $\mu$g of total RNA were fractionated on 1% agarose gel, blotted on to nylon membrane and hybridized with random primed probe using Quickhyb solutions (Stratagene). After washing, membranes were exposed to Kodak films for 6 to 72 hours. As a result of the Northern blot assay, pituitary tumor specific signals were detected for 2 bands. DNA sequence analysis revealed that one sequence was homologous with Insulin-induced growth response protein, while the another 396 base pair fragment (amplified using 5'-AAGCTTTTTTTTTTTG-3' [SEQ. ID. NO.:11] as the anchored primer and 5'-AAGCTTGCTGCTC-3' [SEQ. ID. NO.:12] as an arbitrary primer) showed no homology to known sequences in the GenBank. This 396 bp fragment detected a highly expressed mRNA of about 1.3 kb in pituitary tumor cells, but not in normal pituitary nor in osteogenic sarcoma cells.

Example 2

Characterization of cDNA Sequence Encoding PTTG

To characterize this pituitary tumor-specific mRNA further, a cDNA library was constructed using mRNA isolated from rat pituitary tumor cells. Poly A+RNA was isolated from pituitary tumor $GH_4$ cells using messenger RNA isolation kit (Stratagene) according to manufacturer's instructions, and was used to construct a cDNA library in ZAP Express vectors (Stratagene). The cDNA library was constructed using ZAP Express™ cDNA synthesis and Gigapack III gold cloning kit (Stratagene) following manufacturer's instructions. The library was screened using the 396 bp differentially displayed PCR product (cloned into TA vector) as the probe. After tertiary screening, positive clones were excised by in vivo excision using helper phage. The resulting pBK-CMV phagemid containing the insert was identified by Southern Blotting analysis. Unidirectional nested deletions were made into the DNA insert using EXOIII/Mung bean nuclease deletion kit (Stratagene) following manufacturer's instructions. Both strands of the insert DNA were sequenced using Sequenase (USB).

Using the 396 bp PCR fragment described in Example 1 as a probe, a cDNA clone of 974 bp (SEQ. ID. NO:1) was isolated and characterized. This cDNA was designated as pituitary tumor-specific gene (PTTG). The sequence of PTTG contains an open reading frame for 199 amino acids (SEQ ID NO:2). The presence of an in-frame stop codon upstream of the predicted initiation codon indicates that PTTG contains the complete ORF. This was verified by demonstrating both in vitro transcription and in vitro translation of the gene product as described in Example 3.

Example 3

In vitro Transcription and Translation of the PTTG

Sense and antisense PTTG mRNAs were in vitro transcribed using T3 and T7 RNA polymerase (Stratagene), respectively. The excess template was removed by DNase I digestion. The in vitro transcribed mRNA was translated in rabbit reticular lysate (Stratagene). Reactions were carried out at 30° C. for 60 minutes, in a total volume of 25 $\mu$l containing 3 $\mu$l in vitro transcribed RNA, 2 $\mu$l $^{35}$S-Methionine (Dupond) and 20 $\mu$l lysate. Translation products were analyzed by SDS-PAGE (15% resolving gel and 5% stacking gel), and exposed to Kodak film for 16 hours.

The results indicate that translation of in vitro transcribed PTTG sense mRNA results in a protein of approximately 25 KD on SDS-PAGE, whereas no protein was generated in either the reaction without added mRNA or when PTTG antisense mRNA was utilized.

Example 4

Northern Blot Analysis of PTTG mRNA Expression

A search of GenBank and a protein profile analysis (using a BLAST Program search of databases of the national center for Biotechnology Information) indicated that PTTG shares no homology with known sequences, and its encoded protein is highly hydrophilic, and contains no well recognized functional motifs. The tissue expression patten of PTTG mRNA was studied by Northern Blot analysis. A rat multiple tissue Northern blot was purchased from Clontech. Approximately 2 $\mu$g of poly A+RNA per lane from eight different rat tissues (heart, brain, spleen, lung, liver, skeletal muscle, kidney, and testis) was run on a denaturing formaldehyde 1.2% agarose gel, transferred to nylon membrane and UV-cross linked. The membrane was first hybridized to the full length PTTG cDNA probe, and was stripped and rehybridized to a human β-actin cDNA control probe. Hybridization was performed at 60° C. for one hour in ExpressHyb hybridization solution (Clontech). Washing was twice 15 minutes at room temperature in 2×SSC, 0.05% SDS, and twice 15 minutes at 50° C. in 0.1% SSC, 0.1% SDS. Exposure time for PTTG probe was 24 hrs, and actin probe 2 hours.

The results of the Northern assay indicate that testis is the only tissue, other than pituitary tumor cells, that expresses PTTG mRNA, and the testis expression level is much lower (2 µg polyA+mRNA, 24 hour exposure) than in pituitary tumor cells (20 µg total RNA, 6 hour exposure). Interestingly, the testicular transcript (about 1 Kb) is shorter than the transcript in pituitary tumors (1.3 Kb), indicating that the mRNA is differentially spliced in testis, and that the 1.3 Kb transcript is specific for pituitary tumor cells.

Example 5

Over-expression of PTTG in NIH 3T3 Fibroblast Cells

Since PTTG mRNA is over-expressed in pituitary tumor cells, whether this protein exerts an effect on cell proliferation and transformation was determined. An eukaryotic expression vector containing the entire coding region of PTTG was stably transfected into NIH 3T3 fibroblasts.

The entire coding region of the PTTG was cloned in frame into pBK-CMV eukaryotic expression vector (Stratagene), and transfected into NIH 3T3 cells by calcium precipitation. 48 hrs after transfection, cells were diluted 1:10 and grown in selection medium containing 1 mg/ml G418 for two weeks in when individual clones were isolated. Cell extracts were prepared from each colony and separated on 15% SDS-polyacrylamide gels, and blotted onto nylon membrane. A polyclonal antibody was generated using the first 17 amino acids of PTTG as epitope (Research Genetics). The antibody was diluted 1:5000 and incubated with the above membrane at room temperature for 1 hour. After washing, the membrane was incubated with horseradish peroxidase-labeled secondary antibody for one hour at room temperature. The hybridization signal was detected by enhanced chemiluminescence (ECL detection system, Amersham).

Expression levels of the PTTG were monitored by immunoblot analysis using the above-described specific polyclonal antibody directed against the first 17 amino acids of the protein. Expression levels of individual clones varied, and clones that expressed higher protein levels were used for further analysis.

Example 6

Effect of PTTG Expression on Cell Proliferation

A non-radioactive cell proliferation assay was used to determine the effect of PTTG protein over-expression on cell proliferation (see, e.g., Mosmann, T., 1983, J. Immunol. Meth., 65:55–63; and Carmichael et al., 1987, Cancer Res., 47:943–946). Cell proliferation was assayed using CellTiter 96TM Non-radioactive cell proliferation assay kit (Promega) according to the manufacturer's instructions. Five thousand cells were seeded in 96 well plates (6 wells for each clone in each assay), and incubated at 37° C. for 24 to 72 hours. At each time point, 15 µl of the Dye solution were added to each well, and incubated at 37° C. for 4 hours. One hundred µl of the solubilization/stop solution were then added to each well. After one hour incubation, the contents of the wells were mixed, and absorbance at 595 nm was recorded using an ELISA reader. Absorbance at 595 nm correlates directly with the number of cells in each well.

Three independent experiments were performed. The cell growth rate of 3T3 cells expressing PTTG protein (assayed by cellular conversion of tetrazolium into formazan) was suppressed 25 to 50% as compared with 3T3 cells expressing the pCMV vector alone, indicating that PTTG protein inhibits cell proliferation (data not shown).

Example 7

PTTG Induction of Morphological Transformation and Soft-agar Growth of NIH 3T3 Cells The transforming property of PTTG protein was demonstrated by its ability to form foci in manslayer cultures and show anchorage-independent growth in soft agar (Table 1). As primary pituitary cells are an admixture of multiple cell types and they do not replicate in vitro, NIH 3T3 cells were employed. For the soft agar assay (Schwab et al., 1985, Nature, 316:160–162), 60 mM tissue culture plates were coated with 5 ml soft-agar (20% 2×DEEM, 50% DEEM, 10% fetal bovine serum, 20% 2.5% agar, melted and combined at 45° C.). 2 ml cells suspended in medium were then combined with 4 ml agar mixture, and 1.5 ml of this mixture added to each plate. Cells were plated at a density of $10^4$ cells/dish and incubated for 14 days before counting the number of colonies and photography. Only colonies consisting of at least 40 cells were counted. Values shown in Table 13 are means±SEM of triplicates.

TABLE 13

Colony Formation by NIH 3T3 Cells Transfected with PTTG cDNA Constructs

| Cell line | Growth in Soft Agar | Efficiency of Colony formation in Soft Agar (%)* |
|---|---|---|
| No DNA | 0 | 0 |
| Vector only | 1.3 ± 0.7 | 0.013 |
| PTTG 3 | 26 ± 4.6 | 0.26 |
| PTTG 4 | 132 ± 26 | 1.32 |
| PTTG 8 | 33 ± 6.0 | 0.33 |
| PTTG 9 | 72 ± 13 | 0.72 |
| PTTG 10 | 92 ± 18 | 0.92 |

*Efficiency of colony formation was calculated as percentage of number of colonies divided by total number of cells.

The results indicate that NIH 3T3 parental cells and 3T3 cells transfected with pCMV vector do not form colonies on soft agar, whereas 3T3 cells transfected with PTTG form large colonies. In addition, focal transformation is observed in cells over-expressing PTTG protein, but cells expressing pCMV vector without the PTTG insert showed similar morphology to the parental 3T3 cells.

Example 8

Assay to Determine Whether PTTG is Tumorigenic In Vivo

To determine whether PTTG is tumorigenic in vivo, PTTG-transfected 3T3 cells were injected subcutaneously into athymic nude mice. $3 \times 10^5$ cells of either PTTG or pCMV vector-only transfected cells were resuspended in PBS and injected subcutaneously into nude mice (5 for each group). Tumors were excised from sacrificed animals at the end of the 3rd week and weighed. All injected animals developed large tumors (1–3 grams) within 3 weeks. The results are shown in Table 14 below. No mouse injected with vector-only transfected cells developed tumors. These results clearly indicate that PTTG is a potent transforming gene in vivo.

TABLE 14

In vivo Tumorigenesis by NIH 3T3 Cells Transfected with PTTG cDNA Expression Vector

| Cell line | No. Animals injected | Tumor formation |
|---|---|---|
| Vector only | 5 | 0/5 |
| PTTG 4 | 5 | 5/5 |

Example 9

Human Carcinoma Cell Lines Express PTTG

The pattern of expression of PTTG in various human cell lines was studied employing a multiple human cancer cell line Northern blot (Clontech). The specific cell lines tested are shown in Table 15 below.

TABLE 15

Human Carcinoma Cell Lines Tested

| | Cell Line | PTTG Expression |
|---|---|---|
| 1 | Promyelocytic Leukemia HL-60 | + |
| 2 | HeLa Cell S3 | + |
| 3 | Chronic Myelogenous Leukemia K-562 | + |
| 4 | Lymphoblastic Leukemia MOLT-4 | + |
| 5 | Burkitt's lymphoma Raji | + |
| 6 | Colorectal Adenocarcinoma SW 480 | + |
| 7 | Lung Carcinoma A549 | + |
| 8 | Melanoma G361 | + |

About 2 µg polyA RNA from each of the 8 cell lines indicated in Table 3 above were placed on each lane of a denaturing formaldehyde 1.2% agarose gel, separated by denaturing gel electrophoresis to ensure intactness, transferred to a charge-modified nylon membrane by Northern blotting, and fixed by UV irradiation. Lanes 1 to 8 contained RNA from promyelocytic leukemia HL-60, HeLa cell line S3, human chronic myelogenous leukemia K-562, lymphoblastic leukemia MOLT-4, Burkitt's lymphoma Raji, colorectal adenocarcinoma SW 480, lung carcinoma A549 and melanoma G361, respectively. RNA size marker lines at 9.5, 7.5, 4 4, 2.4, and 1.35 kb were indicated in ink on the left margin of the blot, and utilized as sizing standards, and a notch was cut out from the lower left hand corner of the membrane to provide orientation. Radiolabeled human β-actin cDNA was utilized as a control probe for matching of different batches of polyA RNAs. A single control band at 2.0 kb in all lanes spotted is confirmatory.

The blots were probed with the full length rat PTTG cDNA probe (SEQ. ID No:1; 974 bp) at 60° C. for 1 hr. in ExpressHyb hybridization solution (Clontech) as described by Sambrook et al., the relevant section of which reference is incorporated herein by reference. See, Sambrook et al., Molecular Cloning: A Laboratory Manual, 2nd. Ed, Cold Spring Harbor Laboratory Press, Cold Spring Harbor, N.Y. (1989). The blots were then washed twice for 15 min at room temperature in 2×SSC, 0.05% SDS, and twice for 15 min at 50° C. in 0.1% SSC, 0.1% SDS. A more detailed description of the remaining experimental procedures masy be found in Pei & Melmed, the relevant section of which is incorporated herein by reference. (See, Pei & Melmed, Endocrinology 4: 433–441 [1997]).

All cells tested by the Northern blot analysis as described above evidenced expression of human PTTG (i.e., PTTG1), including lymphoma, leukemia, melanoma and lung carcinomas, among others.

Example 10

Molecular Cloning of Human PTTG cDNA

A human fetal liver cDNA library (Clontech, Palo Alto, Calif.) was screened as described by Maniatis et al. (Maniatis et al, Molecular cloning, Cold Spring Harbor Press, 1989), using a radioactively labeled cDNA fragment of the entire rat PTTG coding region as a probe. The cDNA inserts from positive clones were subcloned into plasmid pBluescript-SK (Stratagene, La Jolla, Calif.), and subjected to sequence analysis using Sequenase kit (U.S. Biochemical Corp., Cleveland, Ohio).

A complete open reading frame containing 606 bp was found in the positive clones. The homology between the nucleotide sequences of the open reading frame and the coding region of rat PTTG is 85%. Amino acid sequence comparison between the translated product of this open reading frame and rat PTTG protein reveals 77% identity and 89% homology. The cDNAs obtained from these clones represents human homologies of rat PTTG. No other cDNA fragments with higher homology were detected from the library.

Example 11

Tissue Distribution of Human PTTG mRNA

Total RNA was prepared using Trizol Reagent (Gibco-BRL, Gaithersburg, Md.) from normal human pituitary glands (Zoion Research Inc. Worcester, Mass.) and fresh human pituitary tumors collected at surgery and frozen in liquid nitrogen. 20 mg total RNA were used for 1% agarose gel electrophoresis. RNA blots (Clontech, Palo Alto, Calif.) derived from normal adult and fetal tissues as well as from malignant tumor cell lines, were hybridized with radioactively labeled human cDNA fragment containing the complete coding region. The RNA isolated from each cell line was transferred onto a nylon membrane (Amersham, Arlington Heights, Ill.), and hybridized with radioactively labeled probe at 55° C. overnight in 6×SSC, 2×Denhardt's solution, 0.25% SDS. The membranes were washed twice at room temperature for 15 minutes each, and then for 20 minutes at 60° C. in 0.5×SSC, 0.1% SDS, and autoradiographed. The autoradiography was carried out using Kodak BIOMEX-MR film (Eastman Kodak, Rochester, N.Y.) with an intensifying screen. The blots were stripped by washing for 20 minutes in distilled water at 95° C. for subsequent probing.

The results from the Northern blot analysis indicated that PTTG is expressed in liver, but not in brain, lung, and kidney of human fetal tissue. In addition, PTTG is strongly expressed in testis, modestly expressed in thymus, and weakly expressed in colon and small intestine of normasl human adult tissue. No expression was detected by Northern analysis in brain, heart, liver, lung, muscle, ovary, placenta, kidney, and pancreas.

The expression of PTTG in several human carcinoma cell lines was also analyzed by Northern blots. In every carcinoma cells examined, PTTG was found highly expressed. The human tumor cell lines tested are listed in Table 16 below.

TABLE 16

Tested Human Tumor Cell Lines

Promyelocytic leukemia HL-60
Epitheloid carcinoma HeLa cell S3
Chronic myelogenous leukemia K-562
Lymphoblastic leukemia MOLT-4
Burkitt's lymphoma Raji
Colorectal adenocarcinoma SW 480
Lung carcinoma A549
Melanoma G361
Hepatocellular carcinoma Hep 3B
Thyroid carcinoma TC-1
Breast adenocarcinoma MCF-7
Osteogenic sarcoma U2 OS
Placenta choriocarcinoma JAR
Choriocarcinoma JEG-3

Example 12

Human PTTG Expression in Normal Pituitary and Pituitary Tumors

RT-PCR was performed as follows. 5 mg total RNA were treated with 100 U RNase-free DNase I at room temperature for 15 minutes. DNase I was inactivated by incubation at 65° C. for 15 minutes The sample was then used for reverse transcription using oligo-dT primer and SuperScript II reverse transcriptase (Gibco-BRL, Gaithersburg, Md.). After reverse transcription, the sample was subjected to PCR amplification with PCR SuperMix (Gibco-BRL, Gaithersburg, Md.) using hPTTG-specific primers and human cyclophilin A-specific primers as an internal control.

Northern blot analysis indicated that the level of expression of PTTG is quite low in normal pituitary as well as in pituitary tumors. Therefore, comparative RT-PCR was used to study the expression of PTTG quantitatively in normal pituitary and pituitary tumors. The results of this study showed that in most of pituitary tumors tested, including non-functioning tumors, GH-secreting tumors, and prolactinomas, the expression level ofPTTG was higher than that of normal pituitary.

Example 13

Stable Transfection of Human PTTG into NIH 3T3 Cells

The complete coding region of hPTTG cDNA was subcloned in reading frame into the mammalian expression vector pBK-CMV (Stratagene, La Jolla, Calif.), and transfected into NIH 3T3 fibroblast cells by Lipofectamine (Gibco-BRL, Gaithersburg, Md.) according to manufacturer's protocol. 24 hours after transfection, the cells were serially diluted and grown in selection medium containing 1 mg/ml G418 for 2 weeks. Individual clones were isolated and maintained in selection medium. Total RNA was isolated from hPTTG-transfected cell lines as well as from control cells in which blank vector pBK-CMV had been transfected. Northern blot was performed to confirm overexpression of hPTTG in transfected cell lines. These cell lines were used in subsequent cell proliferation assay as well as in vitro and in vivo transformation assay.

Example 14

Cell Proliferation Assay

A cell proliferation assay was performed using the Cell-Titer 96 non-radioactive cell proliferation assay kit (Promega Medicine, Wis.) according to the manufacturer's protocol. 5,000 cells were seeded in 96-well plates and incubated at 37° C. for 24–72 hours. Eight wells were used for each clone in each assay. At each time point, 15 ml of dye solution was added to each well and the cells were incubated at 37° C. for 4 hours. After incubation, 100 ml solubilization/stop solution were added to each well, and the plates incubated overnight at room temperature. The absorbance was determined at 595 nm using an ELISA plate reader.

Control and hPTTG-overexpressing NIH 3T3 cells were used to perform this assay. The results indicated that the growth of cells transfected with the PTTG-expressing vector was suppressed by 30~45% as compared with cells transfected with blank vector. These results clearly show that the PTTG protein inhibits cell proliferation.

Example 15

In Vitro and In Vivo Transformation Assay (a) In vitro Transformation Assay Control and hPTTG-transfected cells were tested for anchorage-independent growth in soft agar; 3 ml of soft agar (20% of 2×DMEM, 50% DMEM, 10% fetal bovine serum, and 20% of 2.5% agar, melted and mixed at 45° C.) were added to 35-mm tissue dishes. 10,000 cells were mixed with 1 ml soft agar and added to each dish, and incubated for 2 weeks until colonies could be counted and photographed.

(b) In vivo Transformation Assay $5 \times 10^5$ cells containing either a blank vector or hPTTG-expressing cells were injected into nude mice. The mice were sacrificed two weeks after injection, and the tumors formed near the injection sites examined.

When the NIH 3T3 cells stably transfected with the PTTG-expressing vector were tested in an anchorage-independent growth assay, these cells caused large colony formation on soft agar, suggesting the transforming ability of PTTG protein.

When the NIH 3T3 cells were injected into nude mice, they caused in vivo tumor formation within 2 weeks after injection. These data indicate that human PTTG, as its rat homologue, is a potent transforming gene.

Example 16

Inhibition of Cell Transformation/Tumor Formation by PTTG C-Terminal Polypeptide Cell lines. NIH 3T3 cells were maintained in high glucose (4.5 g/L) DMEM (Gibco-BRL) supplemented with 10% fetal bovine serum. HeLa cells were maintained in low glucose (1 g/L) DMEM (Gibco-BRL) supplemented with 10% fetal bovine serum (FBS). T-47D and MCF-7 cells were maintained in high glucose DMEM (Gibco-BRL) supplemented with 10% fetal bovine serum and 0.01 mg/mL bovine insulin (Sigma). All cell lines were obtained from American Type Culture Collection (ATCC).

Site-directed mutagenesis and stable transfection of human and mutant PTTG into NIH 3T3 cells. Point mutations on the proline-rich domain(s) of wild type human PTTG polypeptide (wtPTTG) were generated by PCR-based site-directed mutagenesis. Two synthetic oligonucleotides, 5'-GATGCTCTCCGCACTCTGGGAATCCAATCTG-3' (SEQ. ID. NO.:5) and 5'-TTCACAAGTTGAGGGG-CGCCCAGCTGAAACAG-3' (SEQ. ID NO.:6), which cause point mutations that result in amino acid sequence changes P163A, S165Q, P166L, P170L, P172A, and P173L in the wtPTTG protein, were used to amplify human PTTG cDNA cloned into pBlue-Script-SK vector (Stratagene).

Amplified mutated cDNA (mutPTTG) was then cloned into mammalian expression vector pCI-neo (Promega). Overexpression of mutPTTG in transfected cells was confirmed by Northern analysis and RT-PCR followed by direct sequence analysis. wtPTTG and mutPTTG were subcloned into pCI-neo, and the vector was used to transfect NIH 3T3 cells as described in Zhang, X., et al. [1999a].

Transactivation assay. wtPTTG cDNA was fused in frame with pGAL4 (Stratagene), designated pGAL4-wtPTTG and was used as template for deletion and mutation analysis; mutPTTG cDNA was also fused in frame with pGAL4 and designated pGAL4-mutPTTG. pGAL4-VP16 was used as a positive control. Experimental plasmids; were co-transfected with pLUC and pCMV-β-Gal (as internal control). Cell lysates were prepared 48 hours after transfection and assayed for luciferase activity as described (Wang, Z. and Melmed, S. [2000]; Sambrook, J., et al., *Molecular Cloning: A Laboratory Manual*, 2d Ed. Cold Spring Harbor Laboratory, Cold Spring Harbor, N.Y., 10.2.1–10.2.6 [1989]).

Constructions of expression vectors for wild type and mutant human PTTG C-terminal polypeptides. To generate wtPTTG and mutPTTG C-terminal polypeptide expression vector, the internai Xba I site of wtPTTG and mutPTTG cDNA and the 3'-portions of these cDNAs were cloned into pCI-neo (Promega, Madison, Wis.) via Xba I and Not I sites. In these clone, the ATG for M147 of full-length PTTG is used as an initiation codon, generating a polypeptide of 56 amino acid residues corresponding to nucleotide positions 147 through 202 of full-length wtPTTG.

Stable transfection of human PTTG C-terminal peptide into tumor cells. Wild type and mutant PTTG C-terminal expression constructs were transfected into HeLa, MCF-7, and T47-D cells with Lipofectin (GIBCO-BRL) according to the manufacturer's protocol. Twenty-four hours after transfection, cells were serially diluted and selected with G418 (1 mg/mL) for 2 weeks. Individual clones were isolated and maintained in selection medium (respective high or low glucose DMEM with 10% FBS, as described above, and G148 [1 mg/mL]), and total RNA was extracted from transfected cells. Expression of wild-type and mutated PTTG-C terminal was confirmed by RT-PCR using two synthetic oligonucleotides, with one specific to the 5'-nontranslational region from vector pCI-neo, 5'-GGCTAGAGTACTTAATACGACTCACTATAGGC-3' (SEQ. ID. NO.:7), and the other to the 3'-translational region of PTTG1 cDNA, 5'-CTATGTCACAGCAAACAGG-TGGCAATTCAAC-340 (SEQ. ID. NO.:8), followed by direct sequence analysis.

In vitro colony formation and in vivo tumorigenesis. NIH 3T3 stable transfectants were tested in vivo as described in Zhang, X., et al. [1999a]. Transfected cells were tested for anchorage-independent growth in soft agar as described Zhang, X., et al. [1999a]. HeLa cells were incubated for 3 weeks and MCF-7 and T-47D cells for 2 weeks. For in vivo assays of tumorigenesis, 1×10⁷ MCF-7 stable transfectants were resuspended in 500 μL MATRIGEL basement membrane matrix (Becton Dickinson, Bedford, Ma.) and were injected subcutaneously into nude mice (three mice for each group). After four weeks, animals were photographed and tumors were excised and weighed.

ELISA of basic fibroblast growth factor (bFGF) in conditioned medium. The concentration of basic fibroblast growth factor (bFGF) concentration in HeLa cell culture medium was assayed using Quantikine HS Human FGF Basic Immunoassay Kit (R&D Systems, Minneapolis, Minn.) according to the manufacturer's protocol. Cells ($1\times10^5$) were plated in 100-mm cell culture dishes. After 72 hours, the culture medium was collected and 200 nL was used for ELISA assay.

Effects of wild type human PTTG and mutant PTTG overexpression on tumor induction. It was previously demonstrated that NIH 3T3 cells overexpressing wild type PTTG formed large colonies in an anchorage-independent growth assay and formed tumors when injected into athymic nude mice, while point mutations in the proline-rich region (P163A, P170L, P172A, and P173L) abrogated formation of colonies and tumors (Zhang, X., et al. [1999a]). Overexpression of wtPTTG and mutPTTG (P163A, S165Q, P166L, P170L, P172A, and P173L) in each transfectant cell line was confirmed by Northern analysis and RT-PCR followed by direct sequence analysis (not shown).

It was further shown that overexpressing PTTG transfectants injected into athymic nude mice caused tumor formation within 2 weeks in all injected animals. Five mice in each of three groups were injected subcutaneously with $3\times10^5$ NIH 3T3 cells transfected with: (1) control cell line (transfected with pGAL4 vector alone); (2) wild type PTTG-overexpressing (wtPTTG); or (3) mutant PTTG-overexpressing (mutPTTG [P163A, S 165Q, P166L, P170L, P172A, and P173L]). After 2 weeks, mice were sacrificed and tumors were excised and weighed. In the mice injected with control transfectants or mutPTTG transfectants, no tumors developed. but mice injected with transfectant cells bearing wtPTTG developed tumors without exception. Tumor weights ranged from 470 to 1500 mg (Table 17)

TABLE 17

Tumor formation by PTTG-expressing NIH 3T3 Cells in Athymic Nude Mice.
Tumor weight (mg)

| Vector | wtPTTG | mutPTTG |
|---|---|---|
| none* | 1500 | none |
| none | 770 | none |
| none | 1250 | none |
| none | 550 | none |
| none | 470 | none |

*none = no detectable tumor.

PTTG exhibits transcriptional activation. Vector pGal4 alone (negative control) did not activate the luciferase (luc) reporter, and a known activation domain, VP16, significantly increased reporter activity about 28-fold. pGAL4-wtPTTG exhibited transactivation properties and induced reporter activity about 22-fold (FIG. 1).

Transcriptional activity of pGAL4-mutPTTG (mutated proline region [P163A, S165Q, P166L., P170L, P172A, and P173L]), other point mutations, as well as a separate deletions (d) of wtPTTG were also tested as indicated in Table 18. In Table 18, the indicated plasmids were co-transfected with pLuc and pCMV-β-Gal into NIH 3T3 cells, and luciferase assays were performed, with β-Gal serving as the internal control. Each value represents triplicate wells from two independent experiments (±SEM); transactivation by wtPTTG was designated 100%. pGAL4-mutPTTG exhibited about 95% transactivating activity compared to pGAL4-wtPTTG, thus confirming the importance of the wtPTTG proline-rich motif for transactivation.

TABLE 18

Transactivation assay of hPTTG mutants.

| Mutant | activation activity (%) (±SEM) |
|---|---|
| pGAL4-wtPTTG | 100 |
| −163 Pro → Ala | 100 ± 10 |
| −166 Pro → Ala | 45 ± 5* |
| −170 Pro → Ala | 100 ± 10 |
| −182 Pro → Ala | 100 ± 10 |
| −152 Glu → Gln | 100 ± 10 |
| −192 Glu → Gln | 50 ± 3* |
| −165 Ser → Ala | 30 ± 3* |
| −165 Ser → Leu | 20 ± 2* |
| −176 Ser → Ala | 100 ± 10 |
| −183 Ser → Ala | 100 ± 10 |
| −184 Ser → Ala | 100 ± 10 |
| -d(1–100) | 100 ± 10 |
| -d(180–202) | 100 ± 10 |
| -mutPTTG | 6 ± 1* |

*p < 0.01

Human PTTG C-terminal peptide expression blocks cell transformation. The critical role of the proline-rich region in transactivation, transformation and tumor formation, as described above, implies that PTTG functions through SH3-mediated signal transduction. If human PTTG1 protein mediates the SH3-related signal cascade, it probably contains at least two functional domains interacting with upstream and downstream signal molecule(s), respectively. A mutant protein containing only one such functional domain could then act in a dominant-negative manner to abrogate wild-type protein function and disrupt signal transduction.

Based on this hypothesis, a truncated PTTG1 mutant peptide, lacking N-terminal amino acid residues 1–146, was introduced into human carcinoma cells An expression construct was used expressing a PTTG-C peptide corresponding to residues 147–202 of the full-length protein, under the control of a CMV promoter. This polypeptide contains the proline-rich domain(s) (residues 163–173; Zhang, X., et al. [1999a]), and when the coding sequence was fused to glutathione S-transferase (GST), it was expressed in *Escherichia coli* as an intact protein with the appropriate molecular weight (data not shown). Mutant expression vector pCIneo-mutPTTG (mutated proline region [P163A, S165Q, P166L., P170L, P172A, and P173L]), as well as the empty vector pCI-neo alone as control, were stably transfected into HeLa, MCF-7, and T-47D human carcinoma cell lines.

Figure 2A:
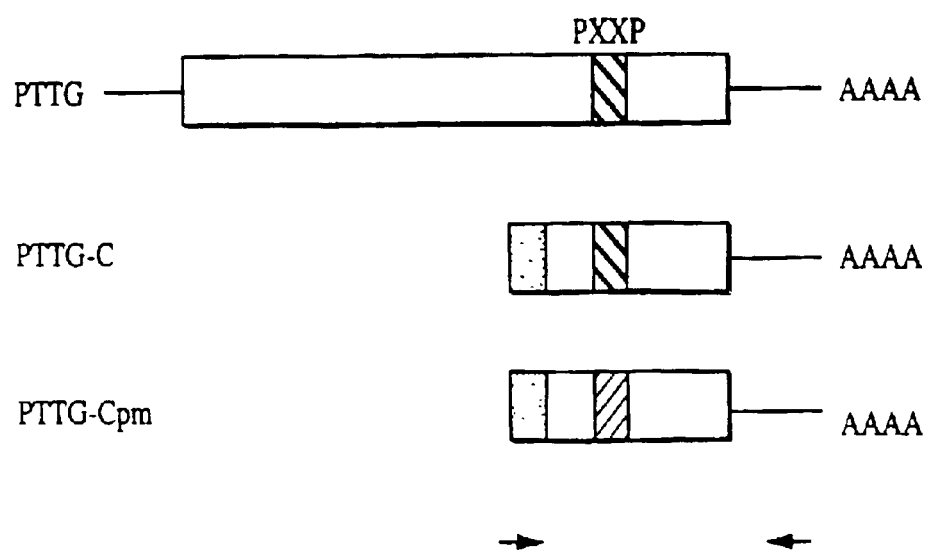
FIG. 2A illustrates expression construct which express a C-terminal peptide of human PTTG protein (PTTGC), corresponding to amino acid residues 147–202 of SEQ. ID. NO.: 4 (i.e., SEQ. ID. NO.: 9), under the control of the CMV promoter (black bar). PXXP represents the proline-rich region(s) of the PTTG-C. A mutant expression vector (PTTG-Cpm), contained point mutations P163A, S165Q, P166L, P170L, P172A, and P173L.
Figure 2B:
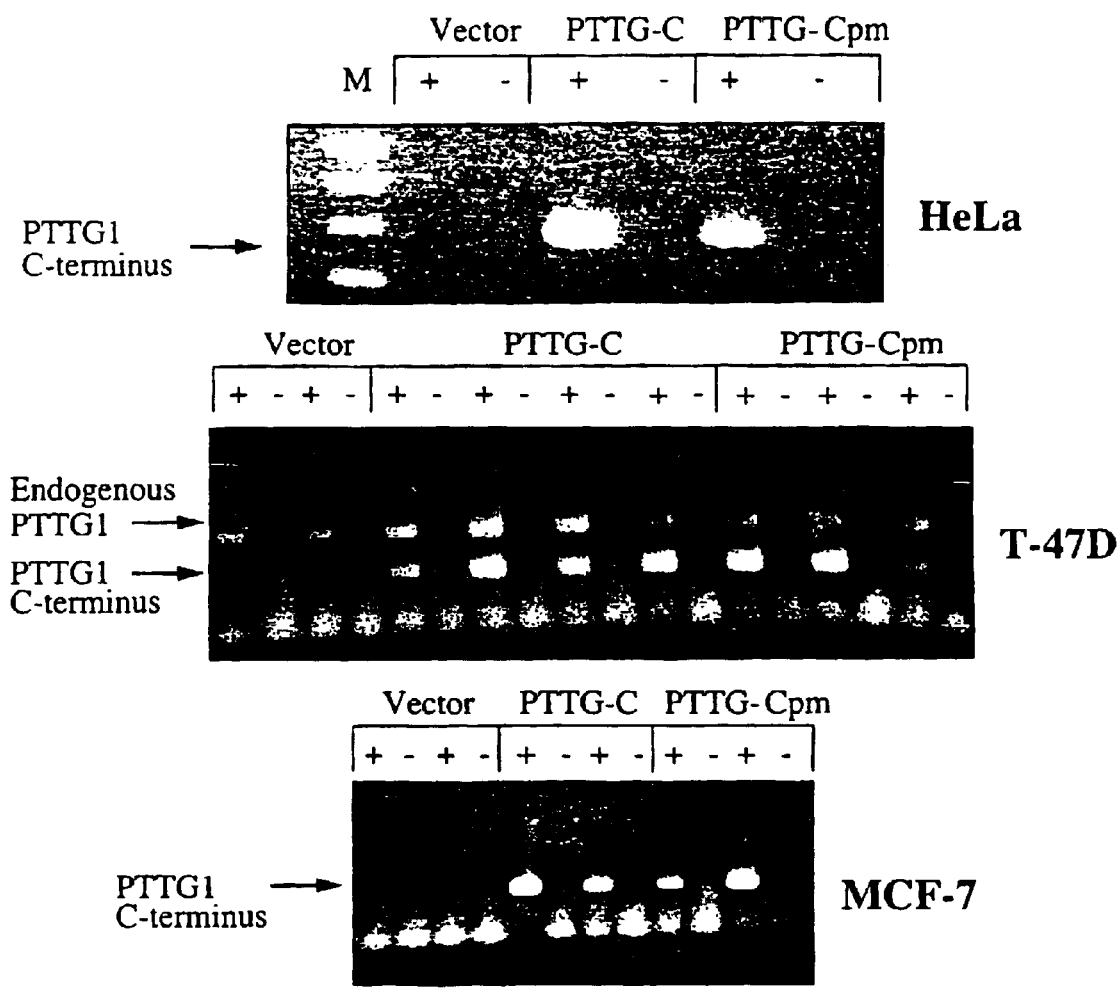
FIG. 2B includes representative 1% agarose gels of RT-PCR products of HeLa (top panel), T-47D (middle panel), and MCF-7 cells (bottom panel), showing PTTG-C and PTTG-Cpm expression. Products from reverse transcription carried out in the presence (+) or absence (−) of RT were used as template in PCR reactions.
Figure 2C:
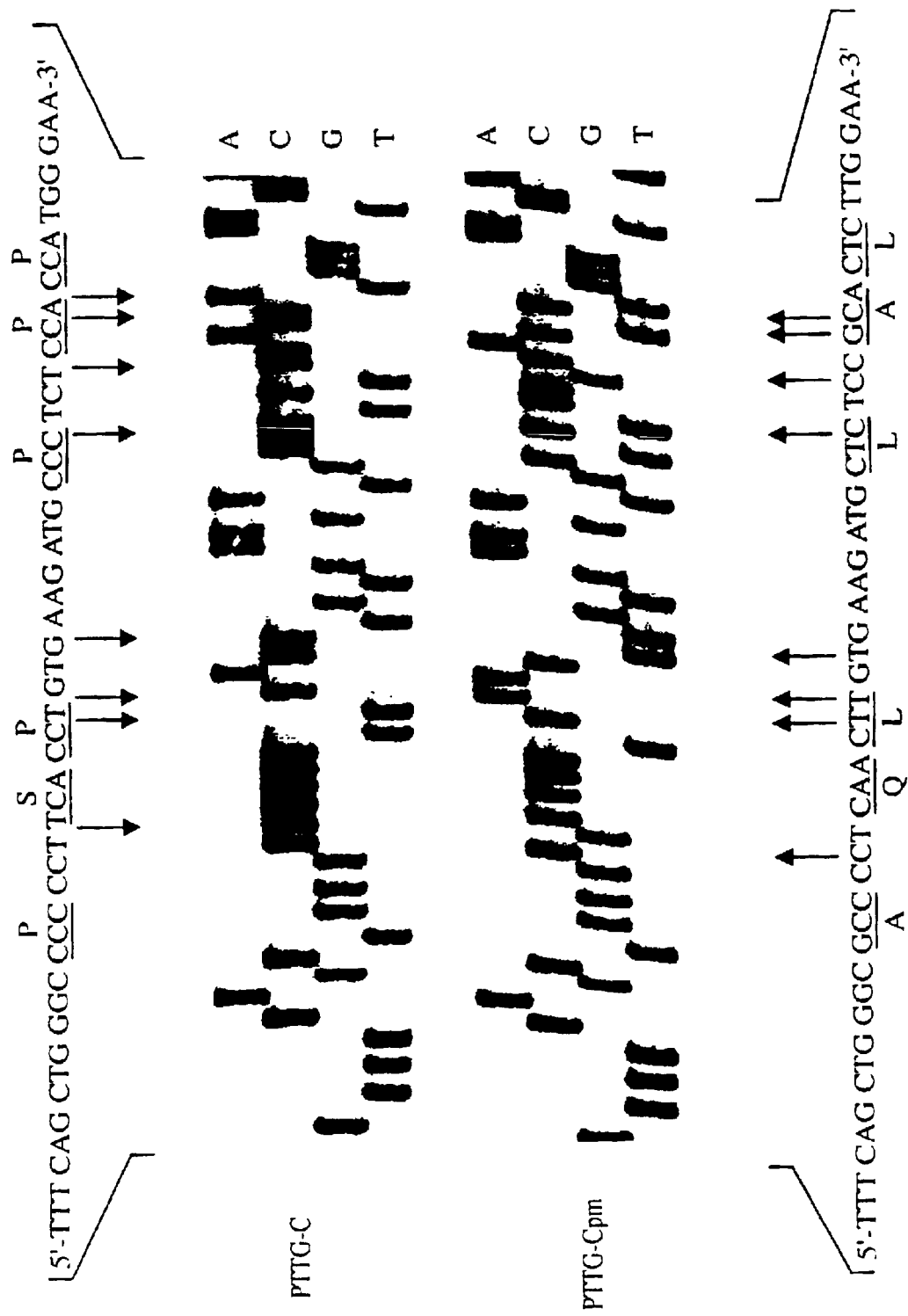
FIG. 2C shows a representative sequencing gel from RT-PCR followed by direct sequencing analysis showing PTTG-C and PTTG-Cpm expression in respective transfectants. Arrows point to nucleotide changes.
Figure 3:
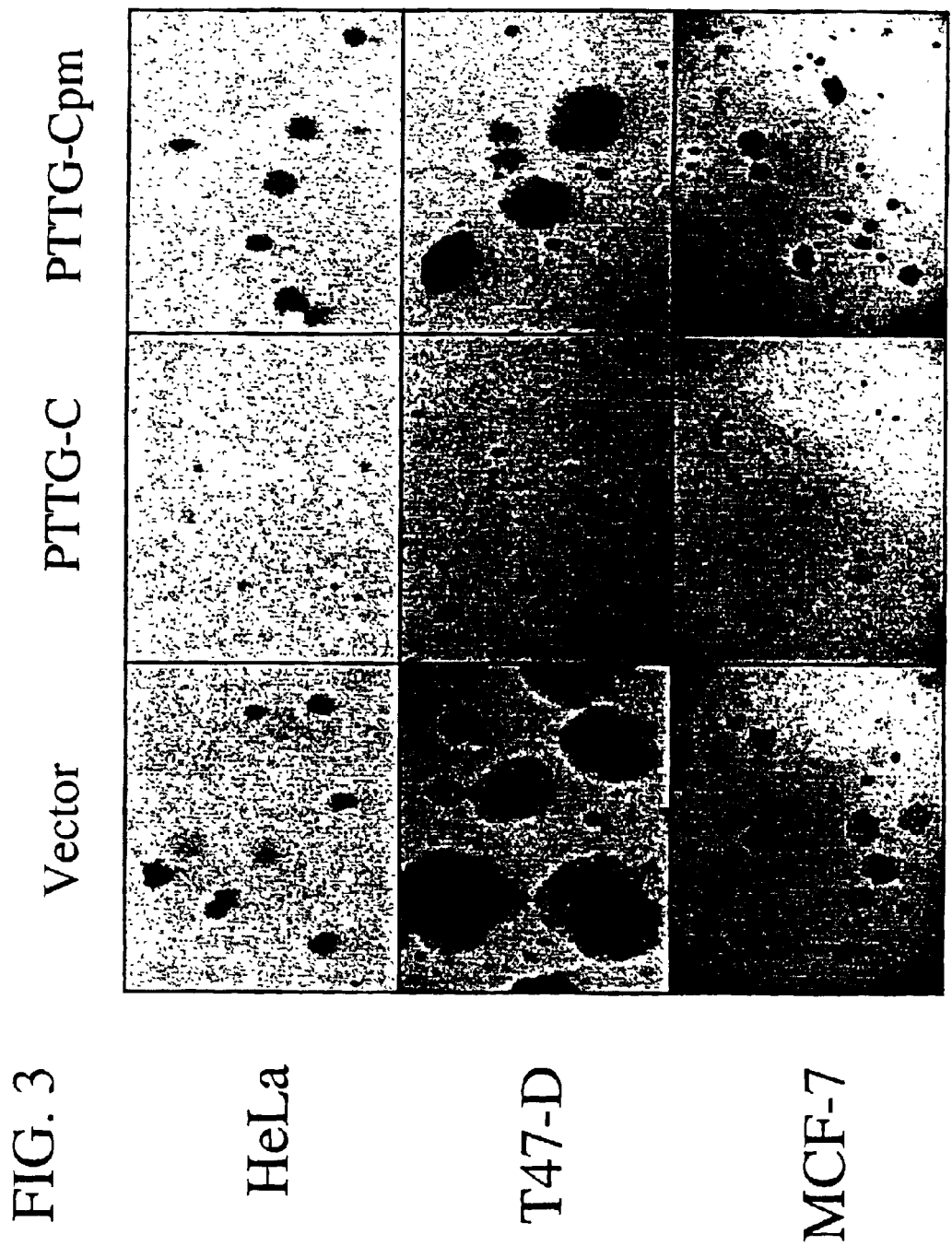
FIG. 3 shows colony formation of HeLa (top row), T-47D (middle row), and MCF-7 (bottom row) cells transfected with PTTG-C or PTTG-Cpm expression vectors on soft agar. "Vector" (left column)shows cells transfected with vector pCI-neo alone; "PTTG-C" (middle column) shows cells transfected with vector pCI-neo containing PTTG C-terminal encoding cDNA; "PTTG-Cpm" (right column) shows cells transfected with vector pCI-neo containing mutant PTTG C-terminal cDNA (P163A, S165Q, P166L, P170L, P172A, and P 173L).

Transfectants expressing wild-type PTTG carboxy-terminal peptide (PTTG-C), PTTG C-terminal mutated in several proline residues (PTTG-Cpm; mutated proline region [P163A, S165Q, P166L., P170L, P172A, and P173L]), and vector (V), were isolated. Expression of each transfectant line was confirmed by RT-PCR, using a primer directed to the 5'-nontranslational region of the expression vector and a primer directed to the 3'-translational region of PTTG mRNA, followed by direct sequence analysis (FIGS. 2A, 2B, and 2C). Transforming abilities of all three of these stably transfected cell lines were tested in an anchorage-independent growth assay, PTTG-Cpm cells were observed to form large colonies, as did control V cells containing the same expression vector but lacking either wild type or mutant C-terminal polypeptide. Each transfectant cell line was plated in three different plates. HeLa was scored on the 21st day and T-47D and MCF-7 on the 14th day. Colonies consisting of 60 or more cells were scored. However, the number and size, of colonies formed by cells expressing PTTG-C were markedly reduced (p<0.01) (FIG. 3). Table 19 (below) summarizes the soft agar colony formation for each cancer cell type.

TABLE 19

Colony Formation by PTTG I C-terminal (PTTG-C) and mutant PTTG C-terminal (PTTG-Cpm) Expressing Cells in Soft Agar.

| Cell Line | Vector | Colonies/$10^4$ Cells (mean ± SEM) |
|---|---|---|
| HeLa | Vector alone | 1465 ± 54 |
| | Vector alone | 2392 ± 55 |
| | PTTG-C | 11 ± 2* |
| | PTTG-C | 6 ± 1* |
| | PTTG-C | 48 ± 3* |
| | PTTG-C | 3 ± 1* |
| | PTTG-Cpm | 1169 ± 77 |
| | PTTG-Cpm | 1097 ± 79 |
| | PITG-Cpm | 2615 ± 76 |
| T-47D | Vector alone | 135 ± 4 |
| | PTTG-C | 46 ± 5* |
| | PTTG-C | 52 ± 2* |
| | PTTG-Cpm | 193 ± 5 |
| | PTTG-Cpm | 106 ± 5 |
| MCF-7 | Vector alone | 287 ± 3 |
| | PTTG-C | 9 ± 3* |
| | PTTG-C | 34 ± 4* |
| | PTTG-Cpm | 236 ± 11 |
| | PTTG-Cpm | 206 ± 4 |

*P < 0.01

Human PTTG C-terminal polypeptide-expressing MCF-7 cells fail to develop tumors in vivo. Stably transfected MCF-7 cell lines were injected ($1 \times 10^7$ cells/per mouse in 500 μL MATRIGEL basement membrane matrix) subcutaneously into athymic nude mice. After four weeks, mice were photographed, killed, and their tumors were excised and weighed. Three mice injected with cells transfected with control vector only developed visible tumors in 4 weeks, while three mice injected with PTTG-C-transfected cells failed to generate tumors. At autopsy, absence of subcutaneous or other peripheral tumor formation was confirmed in the mice receiving PTTG-C transfected cells. Three mice injected with PTTG-Cpm-transfected cells also developed tumors after 4 weeks, which were similar in size to those developed in mice injected with control vector-transfected cells, indicating that the mutated PTTG-C-terminal polypeptide lost its ability to abrogate endogenous PTTG function (Table 20).

TABLE 20

Tumor formation by PTTG-C expressing MCF-7 Cells in Athymic Nude Mice.

| | Tumor weight (mg) | |
|---|---|---|
| Vector | PTTG-C | PTTG-Cpm |
| 212 | none* | 185 |
| 235 | none | 196 |
| 209 | none | 203 |

*none = no detectable tumor.

These results show that overexpression of the PTTG C-terminal peptide caused cancer cells to lose their abilities for in vitro cell transformation and ex vivo tumor growth. Also, the importance of proline-rich regions is further confirmed here, since PTTG C-terminal peptide containing point mutations of these proline residues failed to interfere with transforming activity or tumor-forming activity in vivo.

Figure 4:
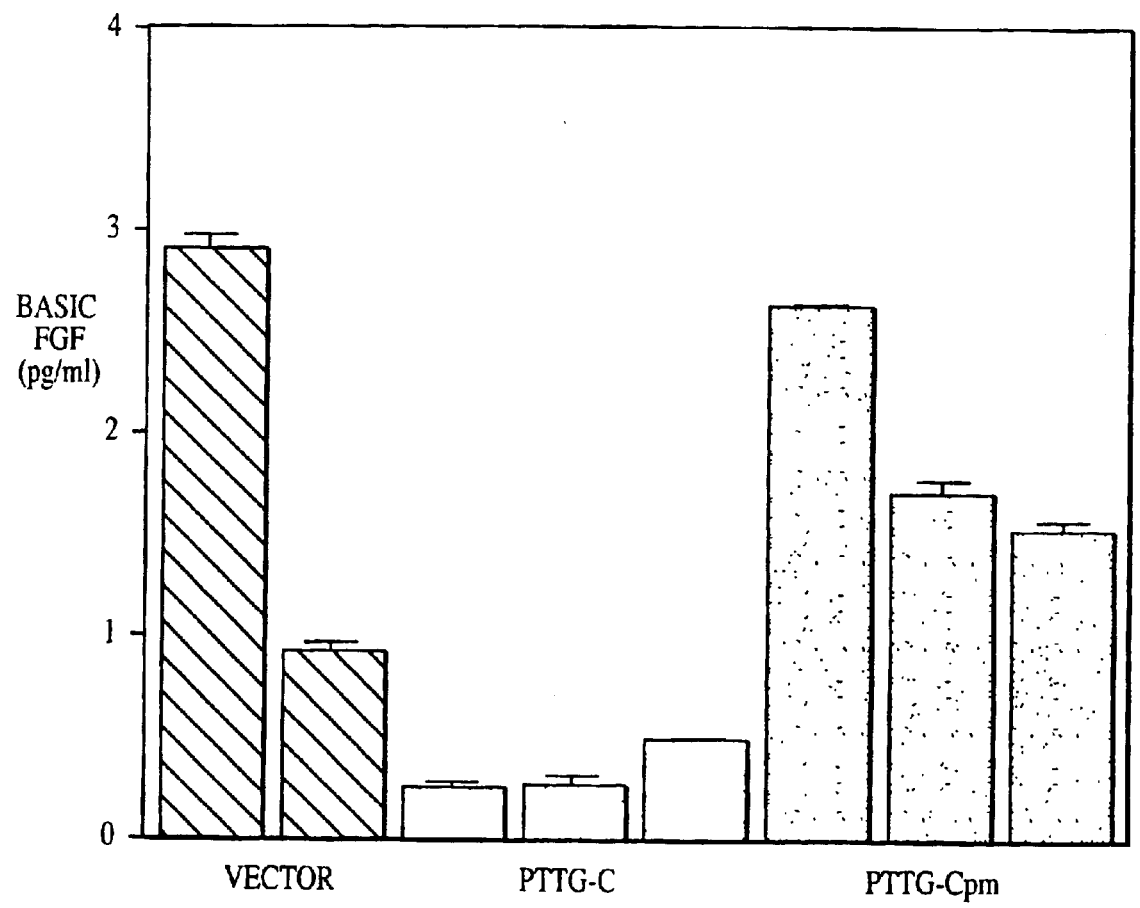
FIG. 4 shows suppression of bFGF secretion by HeLa cells expressing PTTG-C peptide. The concentration of bFGF in conditioned medium derived from transfectants cultured for 72 h as measure by ELISA. "Vector" (two left-most bars) indicates medium conditioned by cells transfected with vector pCI-neo alone; "PTTG-C" (three middle bars) indicates medium conditioned by cells transfected with vector pCI-neo containing wtPTTG-C-terminal encoding cDNA, "PTTG-Cpm" (three right-most bars) indicates medium conditioned by transfected with vector pCI-neo containing mutant PTTG C-terminal encoding cDNA (P163A, S165Q, P166L, P170L, P172A, and P173L).

Suppression of bFGF secretion and PRL expression by PTTG-C peptide. As cells expressing wild-type human PTTG-C terminal peptide had markedly reduced colony forming ability on soft agar and were also unable to induce solid tumor growth in vivo, expression of bFGF was tested in HeLa transfectants. An enzyme-linked immunoabsorbent assay (ELISA) was performed to examine bFGF levels in conditioned medium derived from 72-hour cultures of HeLa transfectants. As shown in FIG. 4, bFGF levels were markedly decreased in conditioned medium derived from PTTG-C DNA-transfected cells than those derived from vector-only and PTTG-Cpm-transfected cells, indicated a suppression of bFGF secretion resulting from the presence of PTTG carboxy-terminal peptide.

Since, the growth rate of solid tumors is directly related to activation of angiogenesis and recruitment of new blood vessels, this shows that, in accordance with the inventive method, the ability for new blood vessel growth can be impaired by the inventive PTTG-C peptides, providing an additional mechanism leading to the failure of in vivo neoplastic cellular proliferation and tumor growth. Experimental tumors do not grow more than 1 or 2 mm in diameter in the absence of angiogenesis. (Folkman, J., N. Engl. J Med. 285:1182–1186 [1971]; Folkman, J., and Klagsburn, M. (1987) Science 235:442–447 [1987]). The human cancer cell lines used in this study form prominent solid tumors (>2 mm in diameter) indicating active angiogenesis.

Moreover, these results imply that additional hormonal regulatory cascades can be affected by the inventive PTTG-C peptides, because reduced bFGF secretion can result in altered expression of bFGF-mediated pathways, for example prolactin (PRL) expression. For example, expression of the same human wild-type PTTG-C-terminal peptide (amino acid residues 147–202 of SEQ. ID. NO.:4) in rat prolactin (PRL)- and growth hormone (GH)-secreting GH3 cells caused markedly reduced PRL promoter activity (about 16-fold decrease), PRL mRNA expression (about 10-fold decrease), and prolactin protein expression (about 72-fold decrease) in comparison to rat GH3 cells transfected with control vector alone or GH3 cells expressing a mutated PTTG1 C-terminal fragment (P163A, S165Q, P166L, P170A, P172A, and P173L; data not shown). Furthermore, a compensatory increase in GH mRNA (about 13-fold increase) and protein (about 37-fold increase) were observed in the PTTG-C-terminal expressing GH3 cells. These observations demonstrate that PTTG carboxy-terminal peptide expressed in GH3 cells alters the hormonal secretory pattern by silencing PRL-gene expression and augmenting GH expression.

We claim:

1. An isolated antibody that specifically binds a PTTG carboxy-terminal peptide selected from the group consisting of:
   (A) peptides having an amino acid sequence consisting of SEQ. ID. NO.:17; and
   (B) peptide fragments of SEQ ID NO. 17 that comprise at least 15 contiguous amino acid residues of SEQ ID NO:17 and include a proline-rich region of SEQ ID NO:17.

2. The isolated antibody of claim 1, wherein the antibody is a monoclonal antibody.

3. The isolated antibody of claim 1, wherein the antibody further comprises a detectable label.

4. The isolated antibody of claim 1, wherein the antibody is a Fab, a Fab', a F(ab')2, or a F(v) fragment of an immunoglobulin.

* * * * *